US012779000B2

(12) United States Patent
Tancowny

(10) Patent No.: US 12,779,000 B2
(45) Date of Patent: Nov. 3, 2026

(54) **PROCESSES FOR EXTRACTING MUSCIMOL FROM *AMANITA MUSCARIA***

(71) Applicant: Psyched Wellness Ltd., Toronto (CA)

(72) Inventor: Brian Tancowny, Beaumont (CA)

(73) Assignee: Psyched Wellness Ltd., Toronto (CA)

( * ) Notice: Subject to any disclaimer, the term of this patent is extended or adjusted under 35 U.S.C. 154(b) by 254 days.

(21) Appl. No.: 18/549,893

(22) PCT Filed: Mar. 14, 2022

(86) PCT No.: PCT/CA2022/050378
§ 371 (c)(1),
(2) Date: Sep. 8, 2023

(87) PCT Pub. No.: WO2022/187974
PCT Pub. Date: Sep. 15, 2022

(65) Prior Publication Data

US 2024/0165180 A1 May 23, 2024

Related U.S. Application Data

(60) Provisional application No. 63/160,721, filed on Mar. 12, 2021.

(51) Int. Cl.
*A61K 36/07* (2006.01)
*A61K 31/42* (2006.01)

(52) U.S. Cl.
CPC .............. *A61K 36/07* (2013.01); *A61K 31/42* (2013.01); *A61K 2236/15* (2013.01); *A61K 2236/17* (2013.01); *A61K 2236/331* (2013.01); *A61K 2236/37* (2013.01); *A61K 2236/51* (2013.01); *A61K 2236/53* (2013.01); *A61K 2236/55* (2013.01)

(58) Field of Classification Search
None
See application file for complete search history.

(56) References Cited

U.S. PATENT DOCUMENTS 8,784,835 B2 * 7/2014 Austin .................. A61K 36/07
548/243

FOREIGN PATENT DOCUMENTS

WO WO-2022132691 A1 * 6/2022 ............. A61K 31/42

OTHER PUBLICATIONS

Falandysz (Fungal Biology (2020), vol. 124, pp. 174-182).*
Chilton (Lloydia (1976), vol. 39, No. 2-3, pp. 150-157—abstract).*
Broadley & Kelly. Muscarinic Receptor Agonists and Antagonists. Molecules. 2001;6:142-193.
Demirbas. Heavy metal bioaccumulation by mushrooms from artificially fortified soils. Food Chemistry. 2001;74:293-301.
Johnston GA. Muscimol as an ionotropic GABA receptor agonist. Neurochem Res. 2014;39(10):1942-1947.
Moss & Hendrickson. Toxicity of muscimol and ibotenic acid containing mushrooms reported to a regional poison control center from 2002-2016. Clin Toxicol (Phila). 2019;57(2):99-103.
PCTCA2022050378. CIPO Examination Notes. May 16, 2022.
PCTCA2022050378. International Preliminary Report on Patentability. Sep. 12, 2023.
PCTCA2022050378. International Search Report. Jun. 15, 2022.
PCTCA2022050378. Written Opinion of the International Searching Authority. May 17, 2022.

* cited by examiner

*Primary Examiner* — Susan Hoffman
(74) *Attorney, Agent, or Firm* — CALYX LAW; Graham Pechenik

(57) ABSTRACT

Disclosed herein are methods of muscimol extraction from *Amanita* mushrooms, and more particularly, enhanced muscimol extraction processes from *Amanita muscaria*, including by distillation, refluxing, and pressing, including processes that increase muscimol content and decrease ibotenic acid content, and which provide liquid and powder extracts useful in preparations for human health.

17 Claims, 12 Drawing Sheets

Ibotenic Acid

Muscimol

PROCESSES FOR EXTRACTING MUSCIMOL FROM *AMANITA MUSCARIA*

CROSS-REFERENCE

This application is a national stage entry under 35 U.S.C. § 371 of International Application No. PCT/CA2022/050378, filed Mar. 14, 2022, which claims priority under PCT Article 8(1) and PCT Rule 4.10 to the U.S. Provisional Patent Application entitled "PROCESSES FOR EXTRACTING MUSCIMOL FROM *AMANITA MUSCARIA*" filed with the U.S. Patent and Trademark Office on Mar. 12, 2021, and assigned App. No. 63/160,721, which is incorporated by reference for all purposes as if fully set forth herein.

TECHNICAL FIELD

Muscimol extraction from *Amanita* mushrooms, and more particularly, enhanced muscimol extraction processes from *Amanita muscaria*, including by distillation, refluxing, and pressing, resulting in liquid and powder extracts useful in preparations for human health.

BACKGROUND OF THE INVENTION

*Amanita muscaria*, also known as the fly agaric, is a mycorrhizal basidiomycete fungus native to temperate and boreal regions of the Northern Hemisphere. It has also been introduced in countries in the Southern Hemisphere. *Amanita muscaria* is the most iconic and arguably best known of all members of the genus *Amanita*, which contains some 600 species.

*Amanita* mushrooms have long been a part of the human diet, and the genus contains well-regarded edible species. The genus also contains some of the most deadly poisonous known mushrooms, together responsible for about 95% of all mushroom fatalities worldwide.

Certain *Amanita* species, with *Amanita muscaria* prime among them, are also known for their psychoactive properties. Ingestion of the *Amanita muscaria* by Siberian tribes of the Kamchatka peninsula and by Indians of the Mexican highlands has been carried out in rituals for centuries. Neurotropic effects were observed by the inhabitants of Siberia and Kamchatka, the Vikings, as well as some North American Indian tribes and the Mayan Guatemalans. While *Amanita muscaria* has been widely used and linked to documented neurotropic effects on mood, it is nevertheless also commonly believed to be a toxic or poisonous mushroom.

*Amanita muscaria* is known to contain several psychoactive compounds as well as some other biologically active substances. Accordingly, chemists, pharmacologists, and ethnobotanists have deployed great efforts in attempts to resolve the chemical composition of these mushrooms and to explain the physiological effects attributed to them for over 100 years. Muscimol ($C_4H_6N_2O_2$) is one of the main psychoactive components of *Amanita muscaria*. Muscimol is known to be an agonist for GABAA receptors (Johnston, Eurochem Res. 2014; 39(10): 1942-7). When binding to a GABAA receptor, muscimol activates the receptor, causing anxiolytic, anticonvulsant, amnesic, sedative, hypnotic, euphoriant, and muscle relaxant properties. Muscimol also may have hallucinogenic effects.

Another psychoactive component of *Amanita muscaria* is ibotenic acid ($C_5H_6N_2O_4$), a conformationally-restricted analogue of the neurotransmitter glutamate that acts as a non-selective glutamate receptor agonist. Ibotenic acid also acts as a neurotoxin; indeed, ibotenic acid has been employed as a "brain-lesioning agent" through cranial injections in scientific research. In typical samples, *Amanita muscaria* contains more ibotenic acid than muscimol. At least some of the ibotenic acid in *Amanita muscaria* is converted by decarboxylation to muscimol in the acid environment of the stomach. Ibotenic acid therefore serves as a prodrug to muscimol. However, if too much ibotenic acid is ingested, it can cause stomach irritation, nausea, diarrhea, sweating and salivation, lethargy and drowsiness, ataxia, and other somatic symptoms, as well as psychological symptoms such as confusion, euphoria, visual and auditory hallucinations, sensations of floating, distortions of space and time, and retrograde amnesia (Moss et al. Clin Toxicol (Phila). 2019; 57(2): 99-103).

Muscarine ($C_9H_{20}NO_2+$) is a further component of *Amanita muscaria*, typically found in smaller quantities than ibotenic acid and muscimol. Muscarine is a nonselective agonist of the muscarinic acetylcholine receptors (Broadley et al., Molecules, 2001; 6(3): 142-193). Muscarine may be toxic in concentrations found in certain mushroom species, but not typically in the concentrations found in *Amanita muscaria.*

Other components of *Amanita muscaria* include heavy metals and other potentially toxic elements and compounds that are absorbed from the soil in the location where a particular mushroom is found growing, and such compounds are therefore variable between specimens depending on where they are collected.

INCORPORATION BY REFERENCE

Each patent, publication, and non-patent literature cited in the application is hereby incorporated by reference in its entirety as if each was incorporated by reference individually. Unless specifically stated otherwise, reference to any document herein is not to be construed as an admission that the document referred to or any underlying information in the document is prior art in any jurisdiction, or forms part of the common general knowledge in the art.

BRIEF SUMMARY OF THE INVENTION

The following presents a simplified summary of some embodiments of the invention in order to provide a basic understanding thereof. This summary is not an extensive overview of the invention. It is not intended to identify key or critical elements of the invention, or to delineate its full scope. Its sole purpose is to present some embodiments of the invention in a simplified form as a prelude to the more detailed description that is presented later.

Muscimol from *Amanita muscaria* has many known and potential health benefits. However, processes for reliably extracting muscimol at high yields and sufficient purity for preparations for human health including pharmaceutical and nutraceutical applications are needed.

In some aspects, provided herein are methods of reducing the ibotenic acid content of an *Amanita muscaria* mushroom extract. In some of any embodiments, the method comprises performing an aqueous extraction of *Amanita muscaria* mushroom biomass in the presence of heat to produce the extract; reducing the pH of the extract to between about 2.0 to about 4.0; and concentrating the extract; wherein the method decreases the ibotenic acid content of the mushroom extract and increases the muscimol content of the extract. In some of any embodiments, the *Amanita muscaria* mushroom biomass is ground into a powder prior to the aqueous extraction. In some of any embodiments, the mushroom biomass is dried to a moisture content of about 1% to about 10%, about 2% to 7%, about 4% to 7%, or about 2%, 3%, or 4% prior to the grinding and aqueous extraction.

In some of any embodiments, the aqueous extraction is performed in water heated to between 65° C. to 120° C., 70° C. to 100° C., or 75° C. to 95° C. for a period of about 0.5 hours to 3 hours, wherein each range is inclusive. In some of any embodiments, the water temperature is maintained at about 75° C. or about 95° C. for about 1 hour or at least 1 hour. In some of any embodiments, the aqueous extract is filtered in the absence or presence of applied pressure. In some of any embodiments, the pH is reduced to about 2.0, about 2.5, or about 3.0.

In some of any embodiments, the concentrating step comprises distilling, refluxing, pressure cooking, or any combination thereof, preferably under light-protected conditions. In some of any embodiments, the distilling comprises vacuum distillation at a pressure of between about 15 psi to about 25 psi (about 1.0 to about 1.7 bar) at a temperature of between about 200° F. to 350° F. (about 93° C. to about 177° C.), wherein each range is inclusive. In some of any embodiments, the distilling proceeds for between about 0.5 hours to 4 hours, or for about 1 hour, 2 hours, 3 hours, or 4 hours.

In some aspects, provided herein are methods of obtaining an *Amanita muscaria* extract. In some of any embodiments, the method comprises applying pressure to a mixture of *Amanita muscaria* mushrooms and heated water through a filter to produce a filtrate; concentrating the filtrate; and reducing the pH of the filtrate to between about 2.5 to 3.5, thereby increasing the muscimol in the extract and decreasing the ibotenic acid in the extract. In some of any embodiments, the method further comprises heating the extract after the reducing step until it is dry. In some of any embodiments, the method further comprises grinding the dried extract.

In some aspects, provided herein are methods of obtaining an *Amanita muscaria* extract, comprising grinding *Amanita muscaria* mushrooms to form a powder; performing an aqueous extraction by heating the powder in water to produce the extract; reducing the pH by adding an acid; concentrating the extract; and collecting the extract; wherein the acidification and concentrating steps reduce ibotenic acid content and increase muscimol content of the extract.

In some of any embodiments, the *Amanita muscaria* extract comprises no stizolobinic acid and no more than 0.09 ppm of cadmium, 0.03 ppm of arsenic, 0.09 ppm of lead and 0.02 ppm of mercury. In some of any embodiments, the *Amanita muscaria* extract comprises less than 18 mg/g of muscimol, less than 600 μg/g muscimol, and less than 20 μg/g ibotenic acid. In some of any embodiments, the *Amanita muscaria* extract comprises less than the limits for respective pesticides in USP 561. In some of any embodiments, the *Amanita muscaria* extract is suitable for oral, sublingual, buccal, mucosal, injectable, intranasal, inhaled, or topical administration. In some of any embodiments, the extract is prepared as a liquid solution, liquid suspension, tincture, beverage concentrate, beverage, tablet, capsule, gelcap, softgel, cream, ointment, gel, foam, or liquid for transdermal application.

In some aspects, provided herein are extracts of *Amanita muscaria* mushrooms obtained by any of the foregoing methods. In some of any embodiments, the extract comprises muscimol and ibotenic acid in a ratio of at least about 20:1 to about 150:1. In some of any embodiments, the extract comprises muscimol and ibotenic acid in a ratio of at least 100:1. In some of any embodiments, the extract comprises at least 15000 μg/g of muscimol. In some of any embodiments, the extract comprises muscimol having a potency of at least 1.5%. In some of any embodiments, extract comprises less than 250 μg/g of ibotenic acid. In some of any embodiments, extract comprises ibotenic acid having a potency of less than 0.025%. In some of any embodiments, the extract is obtained as a liquid distillate. In some of any embodiments, the extract is obtained as a ground powder.

In some of any embodiments, the extract comprises a muscimol purity of at least 90%. In some of any embodiments, the extract comprises no stizolobinic acid and no more than 0.09 ppm, 0.03 ppm, 0.09 ppm and 0.02 ppm of the ingredients of cadmium, arsenic, lead and mercury, respectively. In some of any embodiments, the extract comprises less than 18 mg/g of muscimol, less than 600 μg/g muscimol, and less than 20 μg/g ibotenic acid. In some of any embodiments, the extract comprises less than the limits for respective pesticides in USP 561. In some of any embodiments, the extract comprises a muscimol purity of 90% or greater.

In some of any embodiments, the extract is standardized to a muscimol potency of between about 0.5% and about 5.0%. In some of any embodiments, the extract is suitable for oral, sublingual, buccal, mucosal, injectable, intranasal, inhaled, or topical administration. In some of any embodiments, the extract is in a liquid solution, liquid suspension, tincture, beverage concentrate, beverage, tablet, capsule, gelcap, softgel, cream, ointment, gel, foam, or liquid for transdermal application.

These and other objects, features, improvements, and advantages of the present invention will be more clearly understood and appreciated from a review of the following detailed description of the disclosed embodiments and examples, and by reference to the appended claims. The foregoing summary has been made with the understanding that it is to be considered as a brief and general synopsis of only some of the objects and embodiments disclosed herein, is provided solely for the benefit and convenience of the reader, and is not intended to limit in any manner the scope, or range of equivalents, to which the appended claims are lawfully entitled.

Additional features of the invention will be described hereinafter which also form the subject of the claims of the invention. It should be appreciated by those skilled in the art that the conception and the disclosed specific methods and structures may be readily utilized as a basis for modifying or designing other structures for carrying out the same purposes of the present disclosure. It should be also realized that such equivalent structures do not depart from the spirit and scope of the invention as set forth in the appended claims.

BRIEF SUMMARY OF THE DRAWINGS

To further clarify various aspects of the invention, a more particular description of the invention will be rendered by reference to certain exemplary embodiments thereof which are illustrated in the included figures. It should be understood and appreciated that the figures depict only illustrated embodiments of the invention and are therefore not to be considered limiting of its scope. They are simply provided as exemplary illustrations of certain concepts of some embodiments of the invention.

Certain aspects of the invention are therefore further described and explained with additional specificity and detail, but still by way of example only, with reference to the accompanying figures in which.

DETAILED DESCRIPTION

Figure 1:
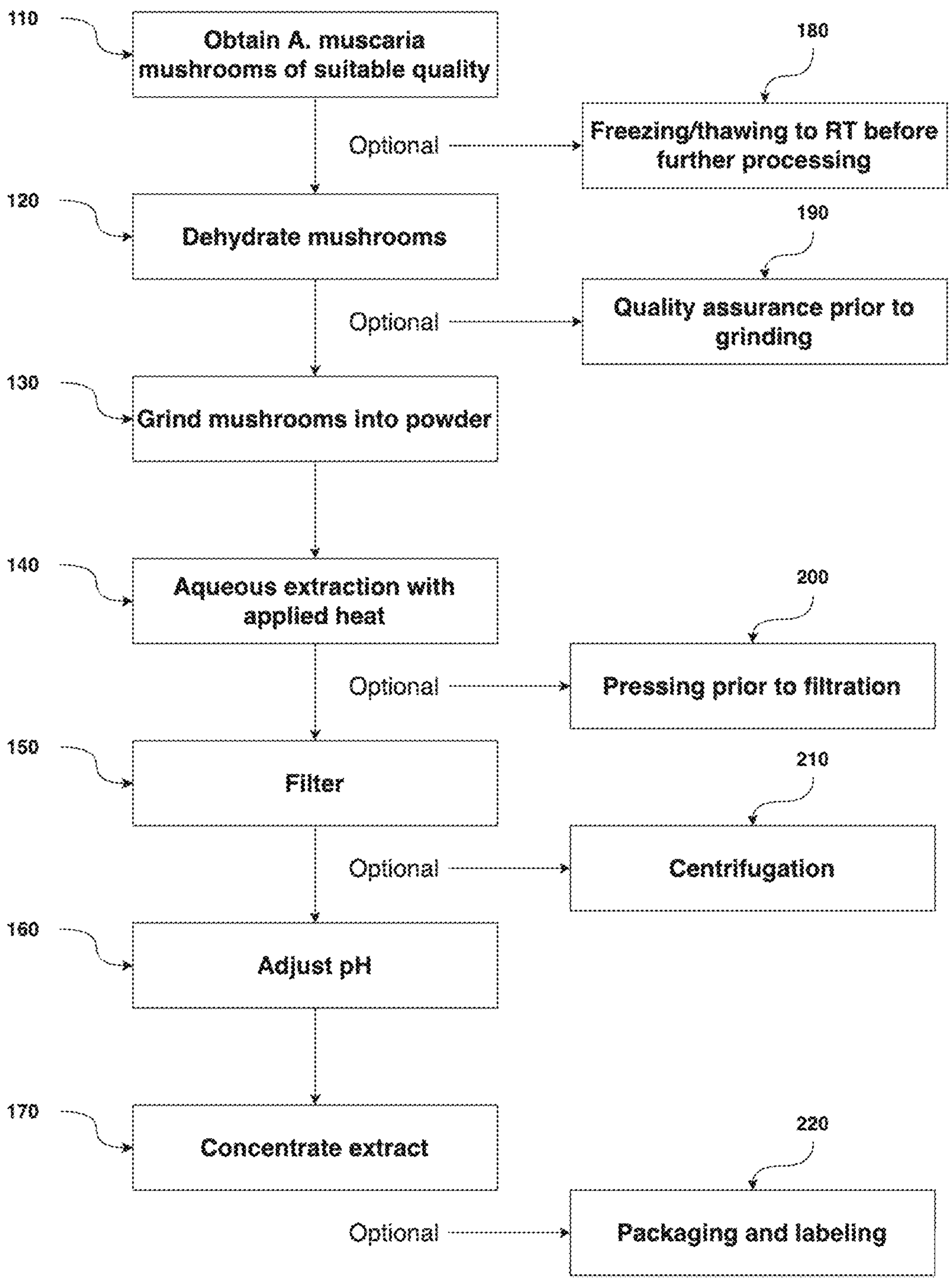
FIG. 1 is a flowchart of an exemplary process for extracting muscimol from *Amanita muscaria*, in accordance with a first embodiment of the invention.

While the embodiments of the present invention are now further described in terms of particular embodiments, examples, and applications, and by reference to the exemplary embodiments that are depicted in the accompanying figures, this description it is not intended to in any way limit its scope to any such embodiments, examples, and applications, and it will be understood that many modifications, substitutions, alternatives, changes, and variations in the described embodiments, examples, applications, and other details of the invention illustrated herein can be made by those skilled in the art without departing from the spirit of the invention, or the scope of the invention as described in the appended claims, including all equivalents to which they are lawfully entitled.

While the methods described and illustrated herein may include particular steps, it should be apparent that other methods including fewer, more, or different steps than those described and shown, and methods providing the particular steps in a different order, are also within the spirit and scope of the invention. The methods and uses of any device or apparatus discussed and associated steps shown herein therefore should be understood as being provided for purposes of illustration, not limitation.

A. General Definitions and Terms

When introducing elements of the present invention or the embodiments thereof, the articles “a,” “an,” “the,” and “said” are intended to mean that there are one or more of the elements. Any reference to an element in the singular is therefore not intended to mean “one and only one” unless specifically so stated, but rather “one or more”; therefore, the term “or” standing alone, unless context demands otherwise, shall mean the same as “and/or.” The terms “comprising,” “including,” “such as,” and “having” are also intended to be inclusive and not exclusive (i.e., there may be other elements in addition to the recited elements). Thus, for example, the terms “including,” “may include,” and “include,” as used herein mean, and are used interchangeably with, the phrase “including but not limited to.” The word “exemplary” is used herein to mean “serving as an example, instance, or illustration.” Any aspect, embodiment, process, or implementation described herein as “exemplary” is therefore not to be construed as necessarily preferred or advantageous over others.

Unless otherwise stated, all measurements, values, ratings, positions, magnitudes, sizes, locations, orientations, configurations, and other specifications that are set forth (either expressly or impliedly) in this specification, including in the figures and in the claims that follow, are approximate, and not exact. They are intended to have a reasonable range that is consistent with the functions to which they relate and with what is customary in the art to which they pertain. Unless otherwise stated, all numbers expressing quantities of ingredients, properties such as concentration, reaction conditions, and so forth, used to describe and claim certain embodiments of the invention are to be understood as being modified in some instances by the term “about.” Where the term “about” is used to modify a value, it means that a range of values that includes the specified value is also encompassed, which a person of ordinary skill would consider reasonably similar to the specified value. Where numerical values may be modified by the term “about,” it will be understood that in some embodiments, such values are modified by “about,” but in other embodiments, such values are within a further degree of precision. In some embodiments, “about” means within a standard deviation using measurements generally acceptable in the art. In some embodiments “about” means within manufacturing tolerances. In other embodiments, “about” means a range extending to +/−10% of the specified value. Accordingly, in some embodiments, the numerical parameters set forth in the written description and attached claims are approximations that can vary depending upon the desired properties sought to be obtained by a particular embodiment. The term “substantially,” when applied to modify a parameter or characteristic herein, will be read in the context of the invention and in light of the knowledge in the art to provide certainty, e.g., by using a standard that is recognized in the art for measuring the meaning of substantially as a term of degree, or by ascertaining the scope as would one of skill.

In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable, taking into consideration manufacturing tolerances, for example. Accordingly, the numerical values presented in some embodiments of the invention may contain certain errors necessarily resulting from the standard deviation found in their respective testing measurements.

Generally, the nomenclature used and procedures performed herein are those known in field(s) relating to that of one or more aspects of the invention, and are those that will be well-known and commonly employed in such field(s). Standard techniques and procedures will be those generally performed according to conventional methods in the art.

Unless defined otherwise, all technical and scientific terms herein have the meaning as commonly understood by a person having ordinary skill in the art to which this invention belongs, who as a shorthand may be referred to simply as "one of skill."

Further definitions that may assist the reader in understanding the disclosed embodiments are as follows; however, it will be appreciated that they will not be used to limit the scope of the invention, which shall be properly interpreted and understood by reference to the full specification (as well as any plain meaning known to one of skill in the relevant art) in view of the language used in the appended claims. That is, the terminology used herein is for the purpose of describing particular embodiments only and is not intended to be limiting.

"*Amanita muscaria*" will be understood to include the *Amanita muscaria* var. *Muscaria* (Euro-Asian fly agaric), *Amanita muscaria* var. *flavivolvata* (American fly agaric), *Amanita muscaria* var. *guessowii* (American fly agaric, yellow variant), and *Amanita muscaria* var. *inzengae* ("Inzenga's" fly agaric); also within the scope and spirit of the invention, and which therefore shall be considered within the definition of *Amanita muscaria* or as equivalents thereof, are such other ibotenic acid and muscimol containing *Amanita* species that are not known to be deadly poisonous, as will be readily appreciated as within the general knowledge in the art.

"Cap" refers to the pileus of a mushroom, including any pieces of universal veil attached thereto, e.g., as warts or irregular patches. Generally the cap of an individual *Amanita* mushroom can be easily separated by hand or other mechanical means from its "stipe" or stem.

"Ibotenic acid" means (S)-2-Amino-2-(3-hydroxyisoxazol-5-yl)acetic acid.

"Muscimol" means 5-(Aminomethyl)-1,2-oxazol-3(2H)-one.

Figure 12:
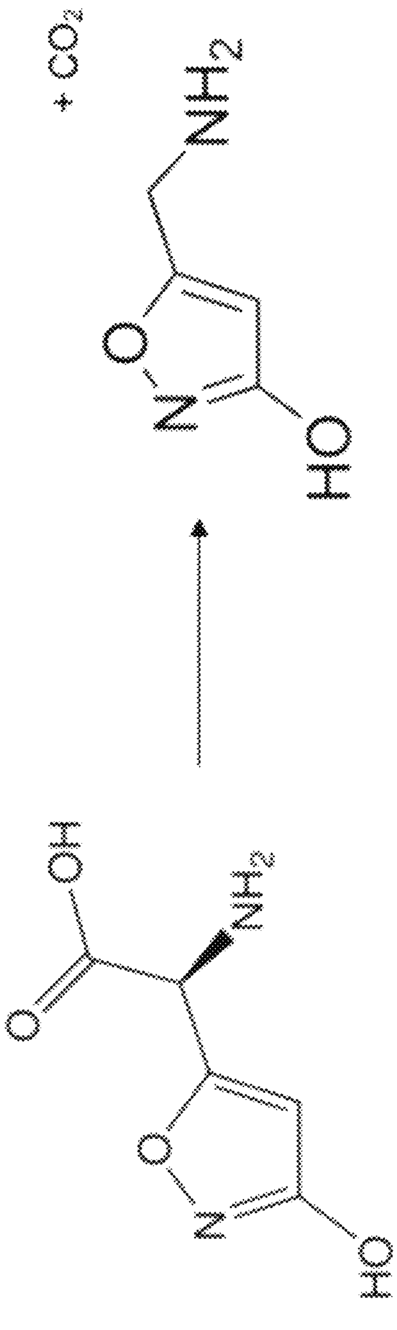
FIG. 12 illustrates the decarboxylation reaction wherein ibotenic acid is converted to muscimol.

"Decarboxylation" refers to a chemical reaction that removes a carboxyl group and releases carbon dioxide ($CO_2$), thereby replacing a carboxyl group (—COOH) with a hydrogen atom (H); e.g., as $RCO_2H \rightarrow RH+CO_2$. The decarboxylation reaction whereby ibotenic acid is converted to muscimol is depicted in FIG. 12.

In accordance with embodiments of the invention, processes are disclosed for extracting muscimol from *Amanita muscaria*. In one example embodiment of the invention, dry or dehydrated *Amanita muscaria* caps are ground and heated in boiled water to convert some of the ibotenic acid in the mushroom caps to muscimol. The mixture is filtered, and acid is added to the filtrate to cause decarboxylation of the ibotenic acid, increasing the conversion of ibotenic acid to muscimol. The acidic mixture is refluxed to remove impurities and further increase the conversion of ibotenic acid to muscimol. Small particles in the filtrate tend to coagulate into larger particles during reflux, facilitating their separation from the filtrate. Distillation has been found to increase the muscimol extracted from *Amanita muscaria* significantly over known prior art techniques.

Depending on the length of the distillation procedure, the muscimol content may be increased after distillation by, for example, at least 25%, at least 30%, at least 40%, at least 50%, at least 60%, at least 75%, at least 100%, at least 150%, at least 200%, or at least 250%, compared to the content before such distillation.

In some embodiments disclosed herein, muscimol purity levels of greater than 90% are achieved, for example a purity of 91.37% muscimol in one such exemplary embodiment. In some embodiments, the purity of a compound can be determined by dividing the weight of the compound by the total weight of the compounds against which its purity is measured (i.e., as a w/w %). For example, in an exemplary embodiment, and using the Certificate of Analysis of Table 3, which shows the weight of compounds of Product Lot Number 0001, the purity of muscimol is determined by dividing the weight of muscimol (16922 μg) by the total weight of the muscimol and the other compounds, i.e., muscarine (1468 μg), ibotenic acid (159 μg/g), and the heavy metals cadmium (0.14 μg), arsenic (2.5 μg), mercury (0.12 μg), and lead (1.6 μg), which in total equal 18553.36 μg, in other words, to divide 16922 μg by 18553.36 μg, which results in a purity of 91.21% muscimol. In some embodiments, a purity of muscimol may be determined by dividing the weight of muscimol (16922 μg) by the total weight of the muscimol and the other compounds (i.e., muscarine and ibotenic acid), but not any heavy metals (e.g., cadmium, arsenic, mercury, or lead). Here, such purity will be $16922/18549$, which equals a purity of 91.23% muscimol.

In some embodiments, a purity of at least about 75%, including about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, and greater than 99.9%, such as 99.99%, and up to 100% may be obtained through utilizing the methods of the invention as disclosed herein. A "substantially pure" preparation of a compound may be defined as a preparation having a chromatographic purity (of the desired compound) of greater than 90%, more preferably greater than 95%, more preferably greater than 96%, more preferably greater than 97%, more preferably greater than 98%, more preferably greater than 99%, more preferably greater than 99.5%, and most preferably greater than 99.9%, as determined by area normalization of an HPLC profile or other similar detection method. Preferably the substantially pure compound is substantially free of any other active compounds, which may cause effect in a subject when administered, and which are not intended to be administered to the subject. In this context "substantially free" can be taken to mean that no compounds other than the target compound are detectable by HPLC or other similar detection method, or that such compounds have a purity below a threshold amount, such as less than 10%, more preferably less than 5%, more preferably less than 4%, more preferably less than 3%, more preferably less than 2%, more preferably less than 1%, more preferably less than 0.5%, and most preferably less than 0.1%, as determined by area normalization of an HPLC profile or other similar detection method.

In some embodiments, potency can be determined by w/w %, e.g., by dividing the weight of a compound to be assessed with the total weight of an extract. For example, in an exemplary embodiment, and using the Certificate of Analysis of Table 3, which shows the weight of compounds of Product Lot Number 0001, the potency of muscimol is determined by dividing the weight of muscimol (16922 μg, i.e., 0.016922 g) per equivalent weight of the extract (1 g) to obtain a potency of 0.016922/1 or 1.69% muscimol, as also shown in Table 7.

In some embodiments, a potency of muscimol in an extract is at least about 0.25%, including about 0.25%, 0.50%, 0.75%, 1.0%, 1.1%, 1.2%, 1.3%, 1.4%, 1.5%, 1.6%, 1.7%, 1.8%, 1.9%, 2.0%, and greater than 2.0%, as may be obtained through utilizing the methods of the invention as disclosed herein. In some embodiments, potency is equivalent to "concentration." In some embodiments, the *Amanita muscaria* extract, which may optionally be further concentrated, is standardized. A "standardized" extract refers to an extract comprising a specified quantity of a standardized ingredient, which may be a bioactive compound such as muscimol. Thus, in embodiments, an amount of the bioactive compound, such as an amount of muscimol, is standardized to a particular concentration (e.g., w/w or w/v % of the extract). In some embodiments, an *Amanita muscaria* extract will be standardized so as to contain by weight percent an amount of muscimol (i.e., mg muscimol per mg or mL of extract, depending on whether such extract is a dry powder or a liquid) of 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, or 5.0% w/w or w/v muscimol. In some embodiments, the *Amanita muscaria* extract will contain by weight percent an amount of muscarine (i.e., mg muscarine per mg extract) of 0.05% or less, 0.05%, 0.06%, 0.07%, 0.08%, 0.09%, 0.10%, 0.11%, 0.12%, 0.13%, 0.14%, 0.15%, 0.16%, 0.17%, 0.18%, 0.19%, 0.20%, 0.21%, 0.22%, 0.23%, 0.24%, 0.25%, 0.26%, 0.27%, 0.28%, 0.29%, or 0.30% w/w or w/v muscarine. Other standardizations w/w or w/v muscimol or muscarine will be as readily known, for example in amounts of between 5.0% and 10.0% or greater than 10% muscimol, of greater than 0.30% muscarine, and also including amounts lower than those explicitly listed above.

Standardization may be accomplished by methods known to those in the art, such as measuring a concentration of compound in an extract to be standardized, determining the concentration of the compound to be standardized, determining an amount of excipient necessary to obtain a desired (standardized) concentration, and then adding the amount of excipient necessary to obtain the desired (standardized) concentration, resulting in a standardized extract. An excipient will be as known by ordinary skill, and may be a dry or liquid excipient, to create a dry powder or liquid standardized extract. Optionally, the concentration of standardized compound in standardized extract may be measured after adding one or more portions of excipient or after the final standardized extract is prepared, to confirm the standardization method and for quality control.

In some embodiments, the *Amanita muscaria* extract is further concentrated so that the bioactive compounds (including, and in particular muscimol) are increased in total concentration from an initial extract, such as an increase in w/w % (for a powder extract) or w/v % (for a liquid extract), in an amount such as by at least 5%, at least 10%, at least 15%, at least 20%, at least 25%, at least 30%, at least 40%, at least 45%, at least 50%, at least 60%, at least 70%, at least 80%, at least 90%, at least 100% (2×), at least 125%, at least 150%, at least 175%, at least 200% (3×), at least 250%, at least 300% (4×), at least 400% (5×), at least 500% (6×), at least 600% (7×), at least 700% (8×), at least 800% (9×), at least 900% (10×), and in amounts of 1,000% or more. Methods of concentrating an extract will be as known in the art, for example by evaporating a portion or an entirety of a solvent to create a volume of concentrated slurry at a desired concentration.

In an example of a second embodiment of the invention, dry or dehydrated *Amanita muscaria* caps are broken into pieces heated in boiled water. The resulting heated *Amanita muscaria* caps are pressed through a filter to extract a filtrate. The filtrate is heated to dehydrate and reduce the volume of the filtrate. The pH of the filtrate is lowered by the addition of an acid and is heated again to concentrate the filtrate, converting the ibotenic acid to muscimol. The resulting filtrate is kneaded and ground.

B. Embodiment 1

FIG. 1 is a flowchart 100 of an exemplary process of the first embodiment of the invention. In the example of FIG. 1, *Amanita muscaria* mushrooms (herein for convenience, "mushrooms") that have been harvested are inspected to ensure that they are of suitable quality (110). Such inspection may identify debris, dirt, and other organic matter (which will be discarded), may be useful in confirming the correct species, and removing mistaken species, especially those that are toxic or poisonous; and/or may aid in determining general "quality," meaning overall appearance, cleanliness, color, damage, apparent age, presence or absence of signs of worms or insects, etc. However, it should be noted, such inspection is not required and, as a result, should not be construed as limiting the invention disclosed herein. Optional step 180 describes freezing the mushrooms for a period of storage prior to further processing, upon which time the mushrooms would be thawed.

Figure 8:
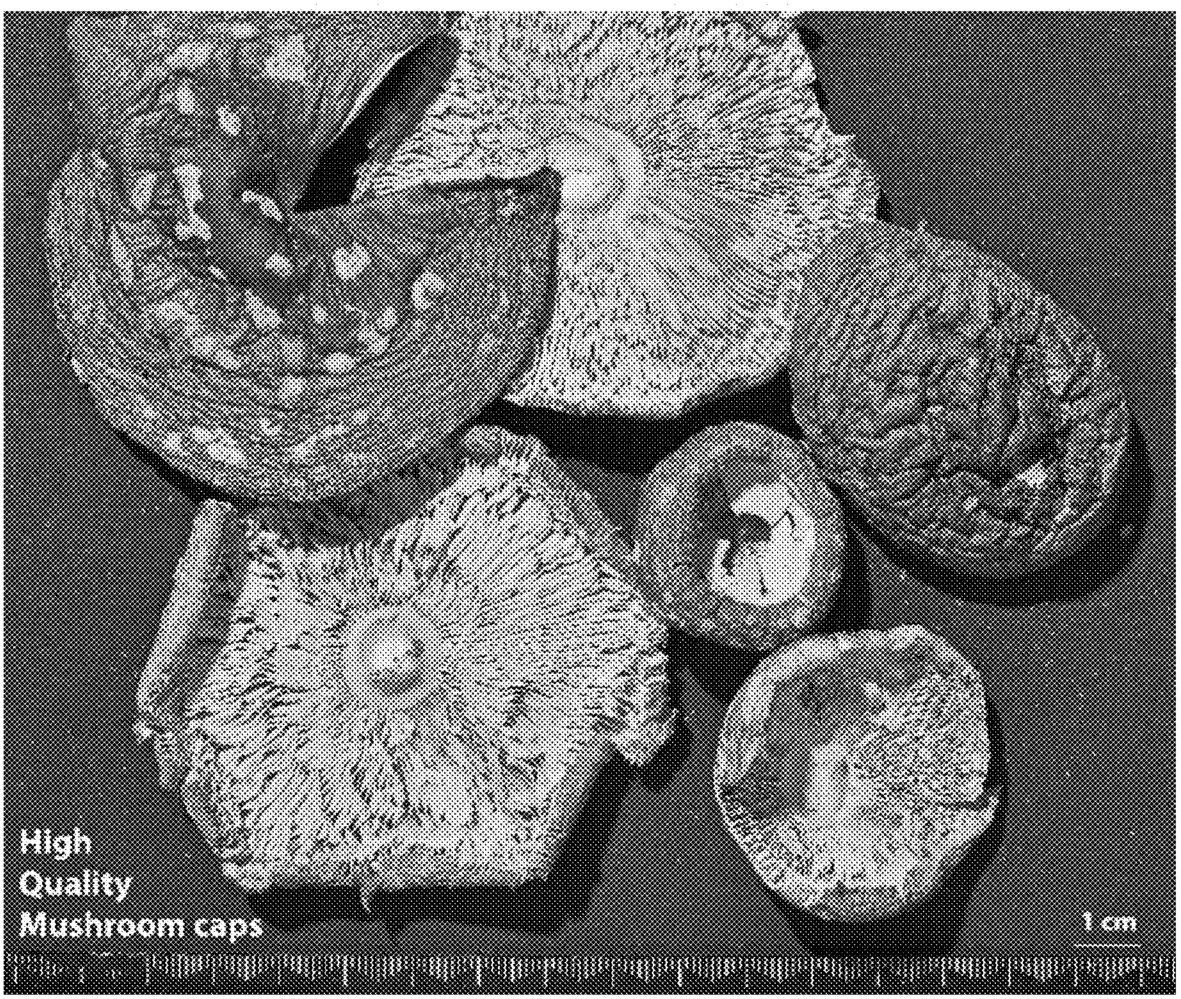
FIG. 8 is an image of an example of high quality mushrooms on visual inspection.
Figure 9:
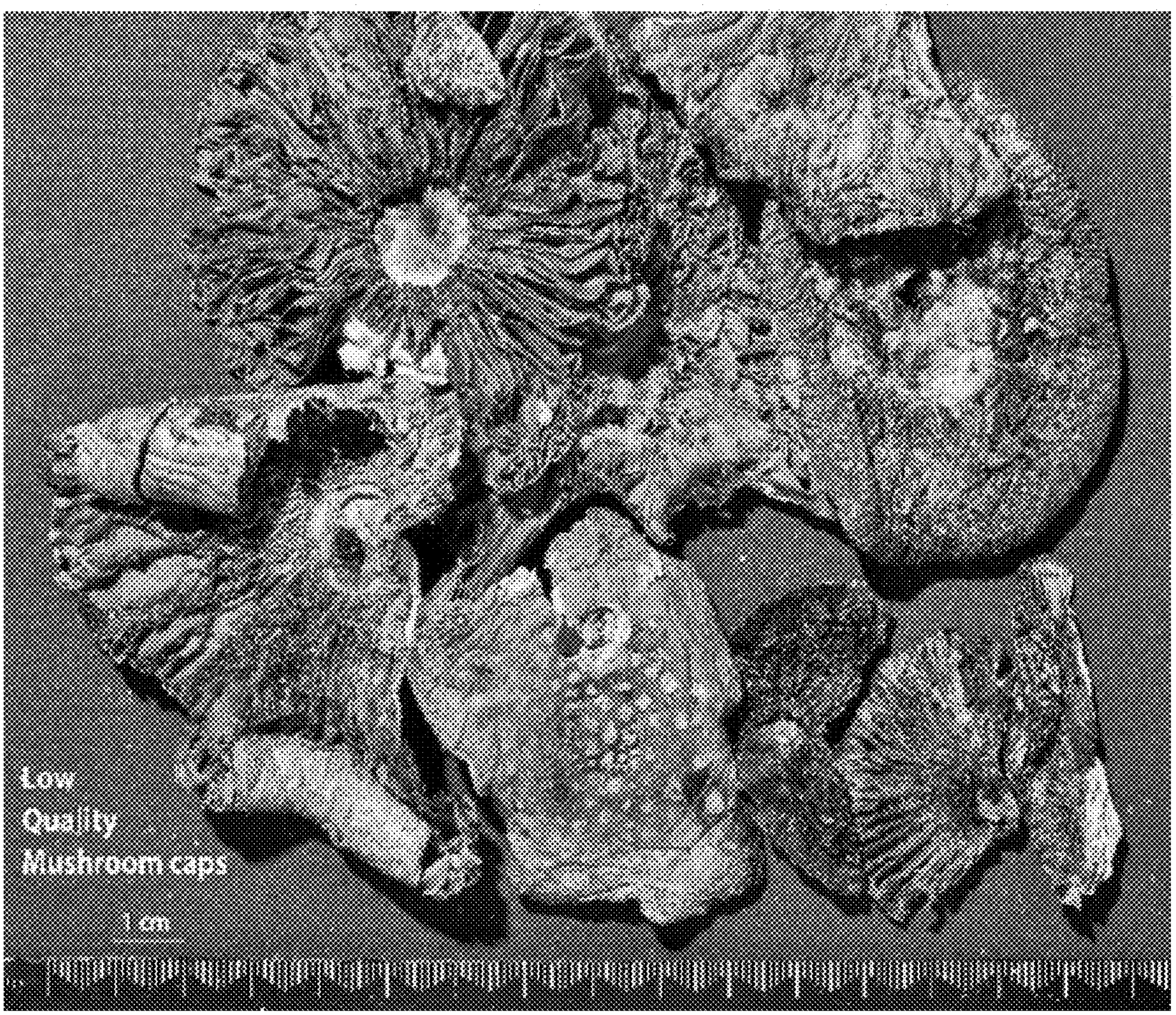
FIG. 9 is an image of an example of low quality mushrooms on visual inspection.

FIG. 8 shows examples of high quality mushroom caps and FIG. 9 shows examples of low quality mushroom caps. As will be immediately evident to one of skill in the art, the high quality mushroom caps retain their natural color, distinct patterns, and shape; while the low quality mushroom caps are visually dessicated, partially decomposed, moldy, include wormholes, are of varying shades of brown, and/or have lost their original shape. In one example, the harvested mushrooms are mature or not yet mature. In some embodiments, mushrooms are not harvested from areas subject to industrial pollution or nuclear fallout.

In embodiments, if the mushrooms are whole (i.e., having a cap and at least a partial stipe), the mushroom caps will be removed from the stipe. In such embodiments, processing preferably uses mushroom caps alone because they have the highest concentration of target compounds in the mushroom, therefore leading to preferable overall yields of muscimol.

In some embodiments, the mushrooms utilized in the process of the invention (FIG. 1) are sufficiently dry, having a moisture content of from about 2% to about 3% moisture by weight. That said, in some embodiments, the mushrooms may have less than 2% or more than 3% moisture by weight. For example, dehydrated mushrooms may have a moisture content of from about 4% to about 7% by weight. If not sufficiently dry when harvested, the mushrooms may be dried (also termed "dehydrated") (120) in a dehydrator or by application of heat in any conceivable method known to those of skill, including but not limited to conduction, convection, or radiation.

It will be appreciated, however, that if dried below 2%, or at too high of a temperature, muscimol and ibotenic acid could be degraded, reducing the final yield of muscimol that will be obtained by the process. The appropriate amount of drying may be determined by practice of ordinary skill for the specific embodiment of the invention being carried out. In one illustrative, non-limiting way of determining an adequate level of moisture content, mushrooms in the desired moisture range easily snap in half. So, dehydration is often completed until the mushrooms are "cracker dry." Meaning, is some embodiments, if the mushroom is merely pliable, and not brittle, it is likely not dry enough. Dryness will be appreciated as sufficient when the mushrooms will be able to be ground into a powder.

That said, drying the harvested mushrooms is merely an optional step, as discussed further below. Thus, embodiments wherein the mushrooms are not dried, or are of a moisture content outside the range disclosed above (e.g., 1%, 2%, 3%, 4%, 5%, 6%, 7%, or greater than 7%, wherein the range is inclusive and each number may be modified by the term "about"), the methods of the invention may still be carried out.

In some embodiments wherein drying is performed (120), drying may be completed at a maximum temperature of 50° C., including 49° C., 48° C., 47° C., 46° C., 45° C., 44° C., 43° C., 42° C., 41° C., 40° C., 39° C., 38° C., 37° C., 36° C., 35° C., 34° C., 33° C., 32° C., 31° C., 30° C., 29° C., 28° C., 27° C., 26° C., 25° C., 24° C., 23° C., 22° C., 21° C., 20° C., or less than 20° C. As it relates to performing the drying specifically, the mushrooms may be dried in a circulated air dehydration unit, a forced air food dryer, or any other such device capable of maintaining a substantially constant temperature set by a user, wherein heating is completed via conduction (direct heating), convection (heating via continuous currents of a gas or liquid), and/or radiation (heating via absorption of heat by a cooler body from a warmer body).

Additionally, drying may, in some embodiments, last from about 24 hours to about 48 hours, including 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, and 48 hours, wherein the range is inclusive and each value will be understood as being both modified and not modified by the term "about." Likewise, in embodiments, heating may be completed for less than 24 hours, such as 20 hours, 16 hours, 12 hours, 8 hours, or less than 8 hours; or greater than 48 hours, such as 56 hours, 60 hours, 65 hours, 72 hours, or 80 hours (inclusive).

In some embodiments, whether or not the mushrooms are dehydrated, they may be sealed in plastic bags or airtight containers and stored in darkness until processing. In such embodiments, the temperature at which the mushrooms are stored should correspond with how soon processing may take place. Generally, mushrooms are stored at between about −25° C. and about 3° C. However, but not to be bound by theory, storage at the warmer temperatures of the aforementioned range is only recommended if processing will imminently occur (such as within about 5 days) because prolonged storage at temperatures above 3° C. may result in a loss of potency and gradual destruction of the mushrooms by macroscopic and microscopic organisms.

In some embodiments, the mushrooms are ground (130). The mushrooms may be ground to a powder that may or may not be a substantially fine powder by a food processor, coffee grinder, blender, or similar device for, in some embodiments, between about 10 seconds, about 20 seconds, about 45 seconds, or about one minute, inclusive.

In an optional step (190), mushrooms are subjected to quality assurance analyses prior to grinding. Although one of skill will readily appreciate how to obtain powder of an appropriate size, visual representations can be found in FIGS. 10 and 11. At this point, in some embodiments, a small batch of the ground powder may optionally be analyzed to determine whether the muscimol, muscarine, and ibotenic acid are within safety and production specifications. In addition, the batch may or may not be analyzed for heavy metal and pesticide content. The analysis may be performed by any device known to those of skill capable of completing such an analysis with one non-limiting example being high performance liquid chromatography tandem mass spectrometry ("HPLC-MS/MS"). In some embodiments, the batch must include at least about 500 micrograms per gram of muscimol to proceed with the method of the invention.

Water (which, in some embodiments, is distilled water) is then obtained, and the pH is determined. If the pH of the water is not about 7, another water sample is selected and tested to confirm the result, and/or the pH of the water is adjusted as needed. One will readily appreciate that if water is contaminated or at an incorrect pH, it may be easiest to simply change to a new source.

The water is then boiled (140) to remove impurities in the water. The mushrooms, which may or may not be ground, are placed in the boiled water (140), and stirred. The temperature of the mixture of water and ground mushrooms is maintained at a temperature of about 95° C. to about 100° C., including about 95° C., 96° C., 97° C., 98° C., 99° C., and 100° C., wherein the range is inclusive and each value may be modified by the term "about."

As it relates to stirring specifically, the mixture is stirred for between about 5 minutes to about 180 minutes, including 5 minutes, 10 minutes, 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, 105 minutes, 110 minutes, 115 minutes, 120 minutes, 125 minutes, 130 minutes, 135 minutes, 140 minutes, 145 minutes, 150 minutes, 155 minutes, 160 minutes, 165 minutes, 170 minutes, 175 minutes, 180 minutes, or greater than 180 minutes, wherein the range is inclusive and each value may be modified by the term "about;" at between 700 rpm and 2500 rpm, including about 750 rpm, 800 rpm, 850 rpm, 900 rpm, 950 rpm, 1000 rpm, 1050 rpm, 1100 rpm, 1150 rpm, 1200 rpm, 1250 rpm, 1300 rpm, 1350 rpm, 1400 rpm, 1450 rpm, 1500 rpm, 1550 rpm, 1600 rpm, 1650 rpm, 1700 rpm, 1750 rpm, 1800 rpm, 1850 rpm, 1900 rpm, 1950 rpm, 2000 rpm, 2050 rpm, 2100 rpm, 2150 rpm, 2200 rpm, 2250 rpm, 2300 rpm, 2350 rpm, 2400 rpm, 2450 rpm, 2500 rpm, and values in between, wherein each value may be modified by the term "about." In some embodiments, the mixture is stirred at 1120 rpm for about 60 minutes.

It will be readily appreciated that, although the length of time for stirring may differ, the duration need only be that which is sufficient to mix the solution, such that the mushroom powder and water form a substantially homogeneous slurry. So, the method of mixing is not important, so long as mixing is adequately completed. Meaning, mixing may be done by hand, via utilization of a stirring utensil, such as a whisk, a spoon, or a spatula; using a stir plate, using an electronic hand mixer, using an electronic mixture having its own arm, or, in some embodiments, using an industrial vat made of a substantially solid material capable of holding the mixture of the invention and possessing at least one agitation means (such as, but not limited to, paddles or arms). All that is required is an apparatus or utensils capable of providing the necessary amount of agitation for the required amount of time.

As it relates to time specifically, as mentioned, agitation may be completed for between about 5 minutes, to at least 120 minutes—the specific amount of time required reflecting the given embodiment being practiced. Meaning, in some embodiments, the duration of time required for agitation may be based on a standard amount of known for that given embodiment, such as but not limited to an embodiment wherein the suggested agitation time is 60 minutes. In other embodiments, agitation may be an iterative process wherein agitation ceases when the mixture forms a substantially homogeneous slurry. As it relates to the invention as disclosed herein, a substantially homogeneous slurry is characterized by substantially uniform dispersion of the mushroom particles within the water, which may be evidenced by the naked eye, and would be immediately apparent to one of skill. However, such uniform dispersion may additionally be determined electronically, using devices known to those of skill capable of determining sample variance.

As mentioned, the water is heated, in some embodiments, to between about 95° C. to about 100° C. Such high temperatures aid in extracting muscimol from the tissue of the mushroom. In some embodiments, the ratio of ground mushroom caps to water may be about 1 gram of mushroom: 40 mL of water, such that 1 gram, 5 grams, 7 grams, 10 grams, 12 grams, 15 grams, 17 grams, 20 grams, 25 grams, 30 grams, 35 grams, 40 grams, 45 grams, 50 grams, 55 grams, 60 grams, 65 grams, 70 grams, 75 grams, 80 grams, 85 grams, 90 grams, 95 grams, or 100 grams of mushroom extract may be combined with 40 mL, 80 mL, 280 mL, 400 mL, 480 mL, 600 mL, 680 mL, 800 mL, 1000 mL, 1200 mL, 1400 mL, 1600 mL, 2000 mL, 2200 mL, 2400 mL, 2600 mL, 2800 mL, 3000 mL, 3200 mL, 3400 mL, 3600 mL, 3800 mL, 4000 mL, respectively.

In some embodiments, the mushroom powder is added to water at about from 65° C. to about 150° C. In some embodiments, the water temperature is about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., about 140° C., about 145° C., about 150° C. In some embodiments, the boiled water is allowed to cool to about 75° C. before adding the ground mushrooms. In some embodiments, the water is heated to about 75° C. before adding the ground mushrooms. In some embodiments, the water is maintained at a temperature of 75° C. prior to adding the ground mushrooms.

In some embodiments, the mixture is then filtered to remove solids (150). Any filter known to those of skill may be utilized, so long as the filter is capable of filtering out both large and small particles. In fact, in some embodiments, a plurality of filters may be used, wherein the pore size decreases with each additional filter. In such embodiments, at least two, at least three, at least four, at least five, or more than five filters may be utilized. This is particularly useful if certain particles of a given size are desired in the filtrate, or to be individually isolated.

In some embodiments, a cheesecloth may be utilized as a filter to remove larger particles while glass wool may be used as a filter to remove smaller particles. In some embodiments, the filtrate may be collected in a flask, such as an Erlenmeyer flask. However, this is merely an exemplary, non-limiting embodiment. As would be apparent to one of skill, any such substantially solid container sufficient to contain the filtrate without leaking may be used for collection. In some embodiments, pressure is applied during the filtration process (200), such as with use of a fruit press.

In other yet embodiments, the mixture may be drawn through the filter(s) by vacuum filtration. It will be appreciated that if the filter does not clog, filtration may take about 15 minutes; however, if the filter gets clogged, filtration may take from about 30 mins to about 60 mins, for example. In another example, the mixture may be placed in a nylon filter bag, such as a 75 micron filter bag, and slowly filtered by a filter press over 60 minutes, for example. In an optional embodiment, the filtrate is centrifuged to separate particulate matter and a supernatant (210).

In some embodiments, the pH of the filtrate may be adjusted by adding an acid to the flask (160). The pH may be reduced from the pH of the filtrate, which is about 7 (the pH of the distilled water) to a pH in a range of from about 5-6, or lower, for example. In some embodiments, the pH is reduced to a pH of about 1.0 to about 4.0. In some embodiments, the pH is reduced to about 1.0, to about 1.5, to about 2.0, to about 2.5, to about 3.0, to about 3.5, or to about 4.0, wherein the range is inclusive. In some embodiments, the acid is acetic acid, boric acid, carbonic acid, citric acid, hydrochloric acid (HCl), hydrofluoric acid (HF), nitric acid, oxalic acid, phosphoric acid, sulfuric acid, or any other compound known to those of skill capable of lowering the pH of the filtrate.

In some embodiments, the acid may be HCl and the pH may be lowered to about 3.0, for example, by the addition of 1M HCl, for example. In some embodiments, the pH may be lowered to about 2.5. Without being bound by theory, the increased acidic environment causes ibotenic acid to convert into muscimol by a decarboxylation reaction, as discussed above. If the mushrooms are not sufficiently dried (to between about 2% to about 3% moisture content), a higher concentration of HCl or other acid may be needed to achieve the same degree of conversion of ibotenic acid to muscimol. A higher concentration of HCl may require use of a safety hood to perform the process, under standard cautionary procedures readily known to ordinary artisans.

In accordance with this embodiment of the invention, the acidic mixture is then refluxed through a distillation apparatus to concentrate the extract (170) by removing contaminants and toxins that are still present in the filtrate. Other mechanisms of concentrating known to one of skill in the art may also be applied to the methods described herein. The contaminants and toxins may be from other mushrooms that may look like *Amanita muscaria* or may be collected with *Amanita muscaria*, some of which may be toxic. For example, *Amanita pantherina* may be present, which generally has higher levels of toxins. One of skill will readily appreciate that the deadly poisonous species of *Amanita*, such as *Amanita phalloides, Amanita ocreata*, and *Amanita virosa*, will not be used in the practice of the invention, and their identification will be generally understood by those of skill.

In some embodiments, the acidified mushroom filtrate or extract is concentrated to accelerate decarboxylation of ibotenic acid into muscimol. In some embodiments, the concentrating step comprises heating the acidified mushroom extract. In some embodiments, the duration of heat exposure is from about 0.5 hours to about 6 hours, wherein the range is inclusive. In some embodiments, the duration of heat exposure is about 0.5 h, 1 h, 1.5 hours, 2 hours, 2.5 hours, 3 hours, 3.5 hours, 4 hours, 4.5 hours, 5 hours, 5.5 hours, or 6 hours. In some embodiments, the heat exposure exceeds 6 hours. In some embodiments, the extract is heated from about 75° C. to about 177° C. (200° F.-350° F.), including about 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C., 116° C., 117° C., 118° C., 119° C., 120° C., 121° C., 122° C., 123° C., 124° C., 125° C., 126° C., 127° C., 128° C., 129° C., 130° C., 131° C., 132° C., 133° C., 134° C., 135° C., 136° C., 137° C., 138° C., 139° C., 140° C., 141° C., 142° C., 143° C., 144° C., 145° C., 146° C., 147° C., 148° C., 149° C., 150° C., 151° C., 152° C., 153° C., 154° C., 155° C., 156° C., 157° C., 158° C., 159° C., 160° C., 161° C., 162° C., 163° C., 164° C., 165° C., 166° C., 167° C., 168° C., 169° C., 170°

C., 171° C., 172° C., 173° C., 174° C., 175° C., 176° C., 177° C., and values in between, wherein each value is modified by the term "about."

In some embodiments, the concentration step comprises application of pressure. In some embodiments, the applied pressure is between about 10 psi and about 25 psi, including at least about 10 psi, 11 psi, 12 psi, 13 psi, 14 psi, 15 psi, 16 psi, 17 psi, 18 psi, 19 psi, 20 psi, 21 psi, 22 psi, 23 psi, 24 psi, 25 psi, and values in between, as would be apparent to one of skill, wherein the values are modified by the term about. In some preferred embodiments, the applied pressure is 15 psi. As is known to one of skill in the art, the pressure described herein can be converted to different units, e.g., 1 psi=6.9 kPa=0.069 bar.

In some embodiments, the concentrating is performed with use of heat and pressure. In some embodiments, distillation assists the conversion of ibotenic acid to muscimol. In some embodiments, refluxing assists the conversion of ibotenic acid to muscimol. In some embodiments, a combination of distillation and refluxing assists the conversion of ibotenic acid to muscimol. In some embodiments, pressure cooking assists the conversion of ibotenic acid to muscimol.

In some embodiments, a condenser may be used, a non-limiting example of which is a Pyrex Graham condenser. As is known in the art, a Graham condenser includes a coolant-jacketed spiral coil running the length of the condenser serving as the vapor-condensate path. The Graham condenser may be attached to another flask, such as a round bottom flask, for example, for collection. The Graham condenser may be placed in a downward position for distillation, so that the acidic mixture enters the condenser at the bottom. The unused neck is stoppered with a plug. In some embodiments, steps are taken to avoid light exposure throughout the process, due to the potential for muscimol degradation. In one non-limiting example, aluminum foil may be wrapped around the round bottom flask and up the condenser part way to lower light intensity inside the round bottom flask during refluxing. However, any such method of reducing light penetration is acceptable, including completing the process in a dark room, setting the flask itself in an enclosure, using an opaque flask that reflects light, etc.

Broadly, the condenser coil is cooled with chilled water pumped in by a pump. The setup is heated and under pressure, such as with a heating mantle. In some embodiments, the distillate is additionally stirred to facilitate even heating. This can be completed with a magnetic stirrer that interacts with the heating mantle, in embodiments wherein such a mantle is utilized, but may also be completed with any such device known to those of skill. Further, heating in and of itself may be completed by any device capable of transferring heat from a heating means to the flask. This can be via a direct flame, via a heating apparatus, such as but not limited to the aforementioned heating mantle, or can be an oven that the flask is placed in with the distillation apparatus protruding therefrom.

Regardless of the heating means, and whether or not the mixture is agitated, high heat is applied (e.g., placing the heating mantle on "high") until distillation begins and then is adjusted so that the rate of distillate collection is about 1 drop per second, for example. In some embodiments, such "high" heat is between about 110° C., to about 130° C., including 111° C., 112° C., 113° C., 114° C., 115° C., 116° C., 117° C., 118° C., 119° C., 120° C., 121° C., 122° C., 123° C., 124° C., 125° C., 126° C., 127° C., 128° C., 129° C., 130° C., and values in between, wherein each value may be modified by the term "about." In some embodiments, the temperature is about 121° C., and the pressure is about 15 psi. In some embodiments, which may or may not be the same embodiments, a practitioner may choose to complete the distillation process in a fume hood since the mixture is acidic.

In one example, distillation is performed for about 0.5 hours to about 6 hours. In some embodiments, distillation is performed for about 5 to about 6 hours. In another example, it is performed for about 2 to about 3 hours. In another example, it is performed for about 3 hours. Distillation for 3 hours, for example, has been found to increase the muscimol content by a significant amount, as is shown through FIGS. 2-5; and to increase the amount of muscimol relative to ibotenic acid, for example, to an extract having a muscimol content of at least 90%. Additionally, it has been discovered that muscimol begins degrading (to a very minimal degree) after being exposed to heat for 3 hours, indicating possible diminishing returns the longer it is exposed to heat. However, in some embodiments, further distillation beyond 3 hours, such as 4 hours, 5 hours, 6 hours, or more than 6 hours, may be advantageous. In some embodiments, the resulting muscimol extract is a liquid.

After filtration in Step 150, the filtrate may be optionally centrifuged. In embodiments wherein centrifuging is completed, it may take place for between about 1 and about 25 minutes, including 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, and values in between, wherein each value may be modified by the term "about;" at between about 2000 to about 6000 rpm, including about 2100 rpm, 2200 rpm, 2300 rpm, 2400 rpm, 2500 rpm, 2600 rpm, 2700 rpm, 2800 rpm, 2900 rpm, 3000 rpm, 3100 rpm, 3200 rpm, 3300 rpm, 3400 rpm, 3500 rpm, 3600 rpm, 3700 rpm, 3800 rpm, 3900 rpm, 4000 rpm, 4100 rpm, 4200 rpm, 4300 rpm, 4400 rpm, 4500 rpm, 4600 rpm, 4700 rpm, 4800 rpm, 4900 rpm, 5000 rpm, 5100 rpm, 5200 rpm, 5300 rpm, 5400 rpm, 5500 rpm, 5600 rpm, 5700 rpm, 5800 rpm, 5900 rpm, 6000 rpm, and values in between, wherein each value may be modified by the term "about." In some embodiments, centrifuging may take place for about 15 minutes at about 4000 rpm at room temperature. In any such embodiments, if there is a resulting pellet of non-soluble and/or fibrous material, it is discarded. The supernatant is then collected.

In some embodiments, the methods described herein produce an extract comprising muscimol and ibotenic acid in a ratio of at least 3:1. In some embodiments, the muscimol to ibotenic acid ratio is from about 3:1 to about 150:1, wherein the range is inclusive and includes values in between. In some embodiments, the muscimol to ibotenic acid ratio is about 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, 100:1, 105:1, 110:1, 115:1, 120:1, 125:1, 130:1, 135:1, 140:1, 145:1, or 150:1. In some embodiments, the extract is packaged and labeled (220). In some embodiments, the extract is stored under conditions protected from light. In some embodiments, the extract is stored in a green, amber, translucent, or opaque container. In some embodiments, an opaque material, such as a foil, such as aluminum foil, is used to cover the container that holds the extract.

C. Embodiment 2

Figure 6:
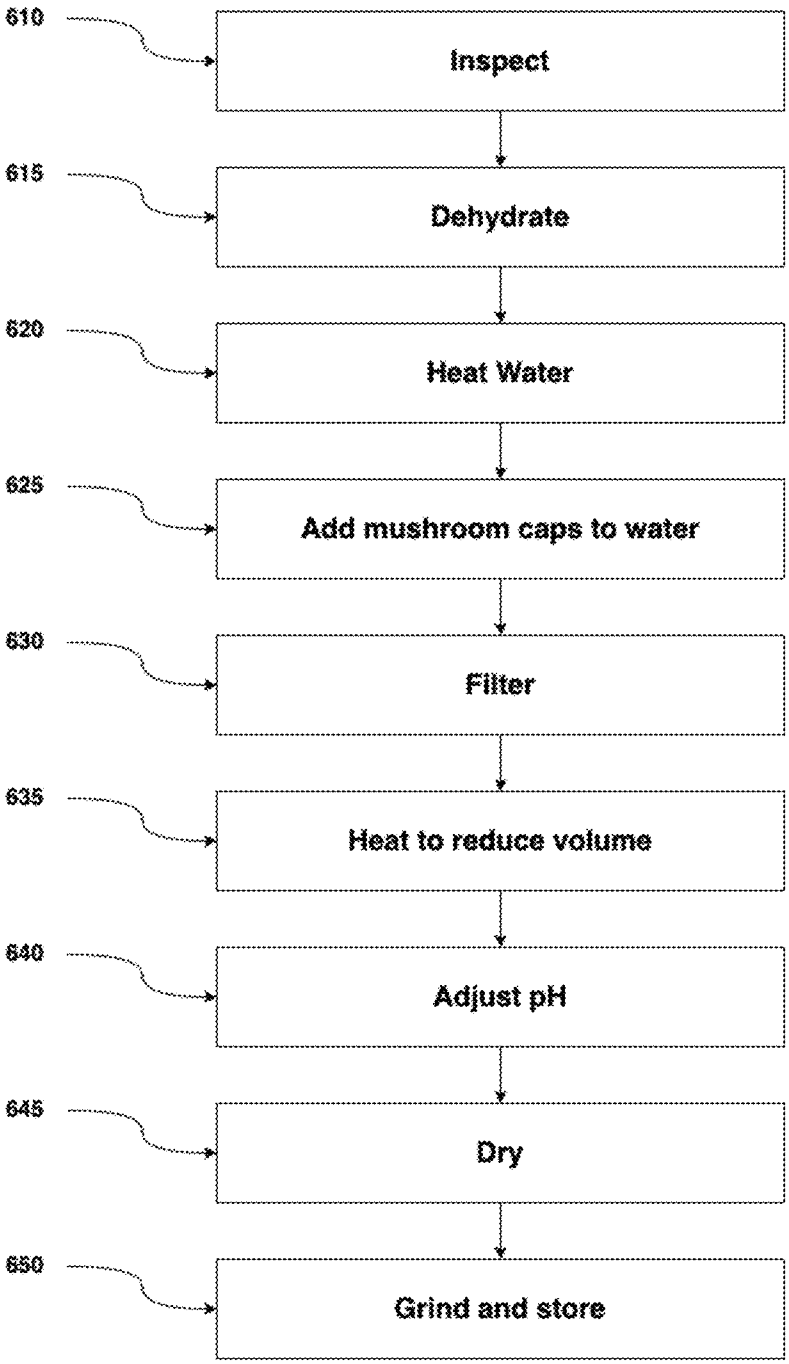
FIG. 6 is a flowchart of an exemplary process for extracting muscimol from *Amanita muscaria* in accordance with a second embodiment of the invention.

In the second embodiment of the invention, a different filtration process is provided to increase yield, where filtration is performed by pressing the ibotenic acid and muscimol containing mushroom material through a filter. The resulting liquid filtrate comprising muscimol is dehydrated and the muscimol is subsequently collected in the form of a powder. FIG. 6 is a flowchart of an example of the second embodiment.

Figure 10:
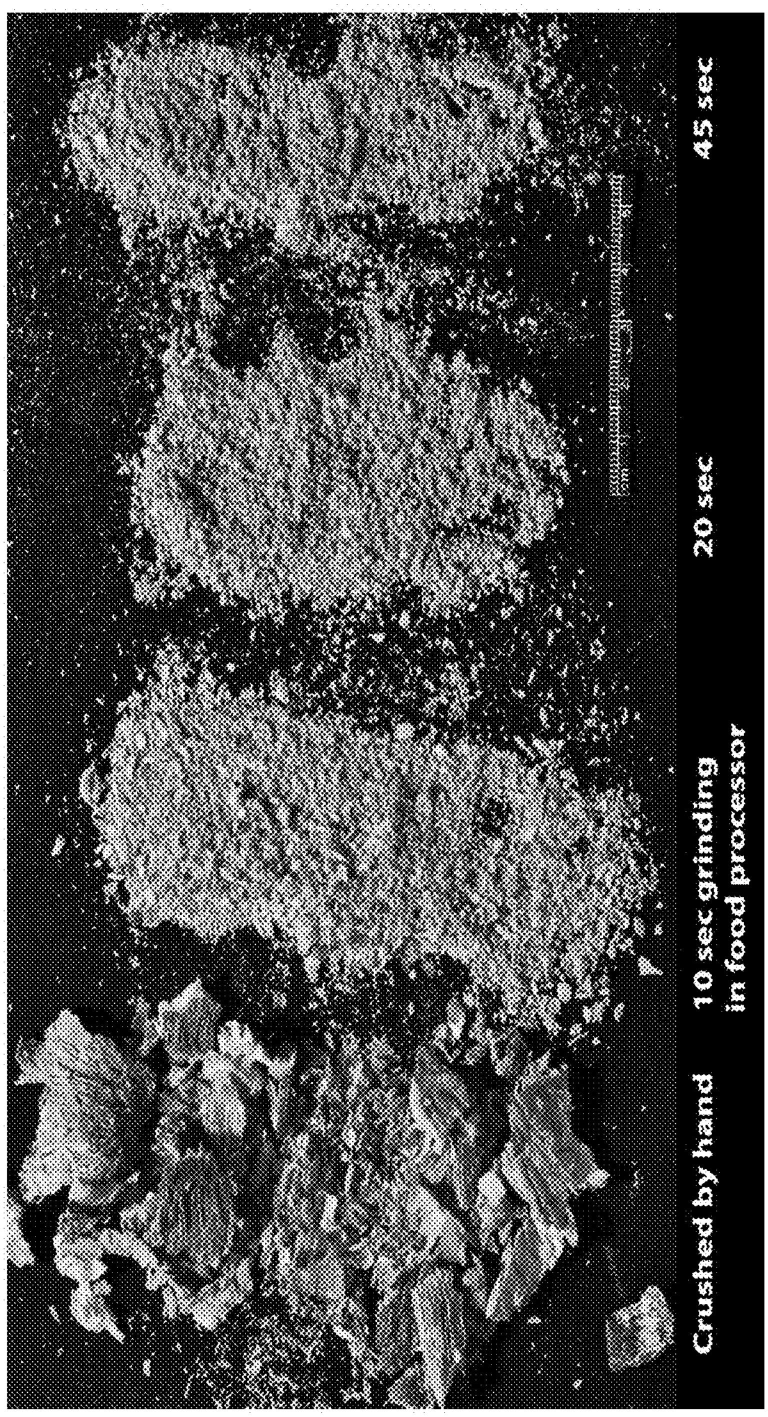
FIG. 10 is an image of examples of mushroom powder generated via grinding for varying durations.

In an example of the second embodiment of the invention, *Amanita* (or generically herein, "mushroom") caps are inspected as in the first embodiment to ensure that they are dry; if not, they are dehydrated, as discussed above, in Step 610 and 615. The mushroom caps are then cut into pieces, or alternatively may be crushed by hand, as shown in FIG. 10. If cut, the pieces may be about 1 cm×1 cm, for example.

As disclosed above, the pH of the water utilized in the invention is then determined. In some embodiments, the water may be any of distilled water, tap water, deionized water, mineral water, or a mixture thereof. So long as the pH is confirmed to be about 7 with a calibrated pH meter, the water is boiled (620). The cut, crushed, or pulverized mushrooms are then placed in the heated water, (625), and may themselves be heated at between about 80° C. to about 105° C., including about 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C., 101° C., 102° C., 103° C., 104° C., 105° C., and values in between, wherein each value is modified by the term "about," for between about 5 minutes to about 25 minutes, including about 5 minutes, about 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, and values in between, wherein each value is modified by the term "about." In some embodiments, the cut, crushed, or pulverized mushrooms are added to the heated water and are themselves heated for about 10 minutes at about 75° C.

In accordance with the second embodiment of the invention, the mushroom pieces are then pressed through a filter in Step 630. The mushroom pieces may be pressed by a fruit press, for example, or otherwise by use of mechanical pressing means, preferably including means of providing leverage or otherwise increasing force (e.g., a crank or double-ratchet mechanism). The mushroom pieces may be placed within a filter bag, such as a micron nylon filter bag, for example, and placed in the press. The pressure of the press may be increased periodically over a period of time, such as every 5 minutes over the course of one hour, for example. In an embodiment, the pressure is increased using operator arm strength, for example. Then, the compressed mushroom mash is removed and the process is repeated until completed.

It has been found that the muscimol content is increased by pressing through the filter. Without limiting the scope of this embodiment of the invention, it is believed that the mechanical forces applied to the mushroom tissue during pressing through the filter breaks up and breaks apart the chitin in the mushroom cells, as well as breaking apart other biomass in the mushrooms, allowing more muscimol and other compounds to be extracted and collected. This includes the ibotenic acid that will be converted into muscimol after addition of acid in subsequent Steps of the process. It will be appreciated that this can also apply to the filtration in the first embodiment above.

The collected filtrate generally has a high water content, e.g., from about 50% to about 70%. So, the filtrate is heated to reduce the water content and decrease the volume in Step 635. The filtrate may be heated in an oven, a microwave oven, or any other such devices known to those of skill useful in transferring a sufficient amount of heat to the filtrate to remove excess water content. The volume may be reduced to about 10% of the original volume of the filtrate, for example.

The pH of the filtrate is then reduced, in Step 640. The pH may be reduced from the pH of the filtrate, which is about 7 (the pH of the distilled water) to a pH in a range of from about 5 to about 6, for example. In some embodiments, the pH is reduced to a pH of about 1.0 to about 4.0. In some embodiments, the pH is reduced to about 1.0, to about 1.5, to about 2.0, to about 2.5, to about 3.0, to about 3.5, or to about 4.0, wherein the range is inclusive. In some embodiments, the acid is acetic acid, boric acid, carbonic acid, citric acid, hydrochloric acid (HCl), hydrofluoric acid (HF), nitric acid, oxalic acid, phosphoric acid, sulfuric acid, or any other compound known to those of skill capable of lowering the pH of the filtrate. In some embodiments, the pH may be reduced to about 3.0 by adding 1M HCl. As above, acidic conditions cause ibotenic acid to more readily convert into muscimol by decarboxylation.

The filtrate at this stage is thick and darkly colored black or nearly black. The filtrate is dried (cured) again, in Step 645, to further reduce the moisture content. The filtrate is dried at a lower power in this Step than in prior Steps so that the muscimol is not degraded. In this Step, the filtrate may be heated in a microwave oven at 80% power at one minute intervals, for example. The filtrate may be stirred in between heating intervals, until the remaining filtrate turns from black to light brown. In an embodiment, heating is for one hour, and while the total time may vary (e.g., due to the power of the heating device used, or the settings thereof), the time will be readily determined by one of ordinary skill. The filtrate may be kneaded to ensure that the filtrate is evenly dried, and not overdried, which could degrade the muscimol. Kneading will allow the determination by touch of the pliability and hardness of the product, and prevent overdrying.

The filtrate is then ground and stored, in Step 650. Depending on the size of the device used to grind the filtrate, the filtrate may need to be cut into pieces for grinding, for example by using a knife. The filtrate may be cut as it is being cooled, for example. The filtrate may then be ground into a fine powder, e.g., as in FIG. 10, using a food processor or coffee grinder, for example, and stored. The powder may be stored in the dark in a sealed container at −15° C., for example.

However, the powder may be stored at temperatures of between about −25° C. to about 3° C., with the specific temperature dependent on the duration of time prior to processing occurring. As mentioned, prolonged storage at warmer temperatures may lead to a loss in potency. Thus, it is only recommended to store at the warmer temperatures in that range if processing will imminently occur (e.g., within about 5 days).

Applications and Uses

*Amanita muscaria* extract prepared in accordance with embodiments of the invention have multiple applications for the improvement of human health, including to reduce pain and treat pain disorders, to reduce and treat inflammation and inflammatory disorders, to benefit immunity and reduce or treat symptoms of immune disorders, including autoimmune diseases and disorders, and for the general improvement of physical health and wellness including relaxation and improvement in sleep, as illustrative and non-limiting examples.

In accordance with one embodiment of the invention, the *Amanita muscaria* extract may be prepared for ingestion in the form of a liquid solution, liquid suspension, tincture, beverage concentrate, or beverage, for example, for the purposes described above. In accordance with another embodiment of the invention, the *Amanita muscaria* extract may be prepared for ingestion in the form of a tablet, a capsule, a softgel, and a gelcap, for the purposes described above, In accordance with another embodiment of the invention, the *Amanita muscaria* extract may be prepared for topical administration in the form of a cream, an ointment, a gel, a foam, and a liquid composition for transdermal application to alleviate pain, itching, and inflammation, as well as to moisturize, rejuvenate, and provide an immune boost to skin and nearby tissue, for example. Methods for preparing such formulations are known in the art.

D. Working Examples

Example 1

Example 1 is an example of the first embodiment of the invention. *Amanita muscaria* ("mushrooms") for use in the process in accordance with an embodiment of the invention were obtained from Vashon Island, Washington. The mushrooms were harvested in the fall of 2020, dried to a moisture content of from about 2% to about 4% by weight, sealed in plastic 4-liter bags, and stored frozen in darkness at −15° C. until used. The mushrooms for the present Example were allowed to thaw to room temperature, were then removed from the plastic bags, and were then inspected to ensure dryness so they can be easily ground to a powder. Dryness was determined in this example by attempting to snap the mushroom caps in half. Mushroom caps in the desired range of dryness snapped in half. This was determined one hour prior to beginning the extraction process.

Mushrooms that were not sufficiently dry were dehydrated in a forced air food dehydrator (internal dimensions, 30 cm×30 cm×30 cm) at 50° C. for 90 minutes. Drying continued until each mushroom was sufficiently dehydrated. Sufficient dehydration in this example is from about 2-3% moisture content by weight.

The dried mushrooms were mixed with distilled water. The pH of the distilled water was first measured after calibration with a pH meter. A Hanna HI 98128 PH meter from Hanna Instruments, Woonsocket, RI, was used. The PH meter was calibrated with pH calibration solutions, including pH 4, pH 7, and pH 10 calibration solutions available from Atlas Scientific, LLC, Queens, NY. The pH of the distilled water was about 4. Since distilled water was stored in a plastic container, the distilled water was boiled to remove any organic material that may have leached into the water from the plastic container. 1000 mL of the distilled water was placed in a 2000 mL Pyrex beaker and boiled at 100° C. for 10 minutes in a microwave oven.

The mushroom caps can be ground to a size range equivalent to about a very coarse to about a very fine grind, which can be performed by a suitable coffee or spice grinder, for example, or an industrial equivalent. Here, the caps were ground by a Jura-Capresso coffee grinder Model No. 501, 120 Volts AC, 100 Watts, 60 Hz, available from The Capresso Company, Montvale, NJ. The caps were ground for 45 seconds, resulting in the appearance in FIG. 10, for example.

The beaker of boiled water was removed from the microwave oven and placed on a heating plate. Twenty-five grams of the ground mushroom caps were added to the hot water and gently stirred with a glass rod for 10 minutes. The temperature was maintained at 95° C. The ratio of mushroom caps to distilled water as 25 grams to 1000 mL water.

The mixture of the ground mushroom caps in the heated water in the beaker was then filtered. A Buchner funnel was set up for vacuum filtration. The Buchner funnel was a QWORK 500 ML Filtering Buchner Funnel Medium Frit (G2) Lab Glassware with standard 24/20 joint and vacuum serrated tubulation (94 mm ID, 100 mm depth), commercially sourced online. The Vacuum filtration was driven by a General Electric Motor Model 5KH45AB49, cycles: 60¼ HP, PH: 1 Form B, 1725 RPM, 110 volts, 4.8 amps, Temp Rise: 40° C., Time Rating: Cont., N.P. 55890-B, Max vacuum: −0.7 bar, available from General Electric, Schenectady, NY.

A 23-gram piece of 10 cm×10 cm×5 cm glass wool was cut in a circular shape approximately the same diameter as the Buchner funnel. It was placed on top of the glass filter in the funnel. The glass wool was a Thomas No. 20A00H747, Catalog No. GLW500 glass wool available from Thomas Sci. Co., Swedesboro, NJ. Four grams of cheese cloth measuring 25 cm×30 cm was folded into four layers and placed on top of the glass wool. The cheese cloth captured larger particles while the glass wool captured smaller particles.

The filter setup was attached to a 1000 ml Erlenmeyer flask. The filter layers were seated by pouring 100 ml of the distilled water that was earlier boiled, though the setup with vacuum turned on. Filtrate was removed from the flask after pouring water through the filters.

To filter the mixture of ground mushroom and water, the mixture was allowed to settle for two minutes in the beaker. The mixture was then slowly decanted into the filter without the ground mushroom powder at the bottom of the beaker to pour into the filter until near the end of the procedure. This reduced clogging and maintained a better flow through the filter. The vacuum pump was turned on to begin to filter the extract, at a pressure of −0.7 bar.

When the extract was filtered, the filter set up as vacuum flushed with 30 ml of the distilled water that was previously boiled. The process yields from about 925 mL to about 975 mL of filtrate in the flask, when performed as a single run. The filtrate appeared cloudy.

The pH of the filtrate was adjusted from the pH of about 7 (the pH of the distilled water) to a pH of about 3.0 by the addition of 1M hydrochloric acid. The hydrochloric acid was obtained from Thermo Fisher Scientific, Hampton, New Hampshire.

After addition of the hydrochloric acid, the filtrate was refluxed through a Pyrex Graham condenser having a coolant-jacketed spiral coil running the length of the condenser serving as the vapor-condensate path. The length of the Graham condenser was 43 cm. The length of the water jacket was 30 cm and it had 24/60 glass joints. The Graham condenser was attached to a 2000 ml round bottom flask for collection. The Graham condenser was in a downward position for distillation. The unused neck was stoppered with a glass 24/40 plug. The Graham condenser was coupled to a Petmate Low Voltage Fountain water pump, Model Number TP 200 LVU, AC 12 volts, 60 Hz., head 0-70 cm.

A round bottom flask was secured to the condenser with burette/test tube clamps from Eisco Lab, Victor, NY, that were attached to a generic 60 cm high ring stand. Aluminum foil was wrapped around the round bottom flask and up the condenser part way to lower light intensity inside the round bottom flask during refluxing. The Erlenmeyer flask was attached to the inlet of the Graham condenser.

The condenser coil was cooled with cold water pumped in by a pump. The setup Graham condenser was heated with a heating mantle/magnetic stirrer. The distillation was performed in a fume hood. Distillation took place at 250° F. (~121° C.) at 15 psi (~1.0 bar). A 2.5 cm magnetic stir bar was placed in the pH distillate to be distilled before starting distillation. During distillation, the magnetic stirring was provided at from about 30 rpm to about 60 rpm, to prevent bumping. The heating level was set on high until the distillation began and was then adjusted so that 1 drop per second was observed and collected. The magnetic stirrer was a 2000 mL model 98-11-B 450 W Huanghua Faithful Instr., Co., Huanghua, China.

The refluxed extract was then distilled for a period of 3 hours. Samples were taken prior to distillation, after 1 hour, 2 hours, and at 3 hours of distillation, as discussed further below. After distillation, the filtrate was cooled to 3° C. in a refrigerator. After about 3 hours of cooling, there was coagulated material suspended in the filtrate. The coagulated material in the filtrate was removed via vacuum filtration through the vacuum filtration setup described above (without the cheesecloth). After filtration, the filter setup was rinsed under vacuum with 30 mL of distilled water into the filtrate.

Figure 7:
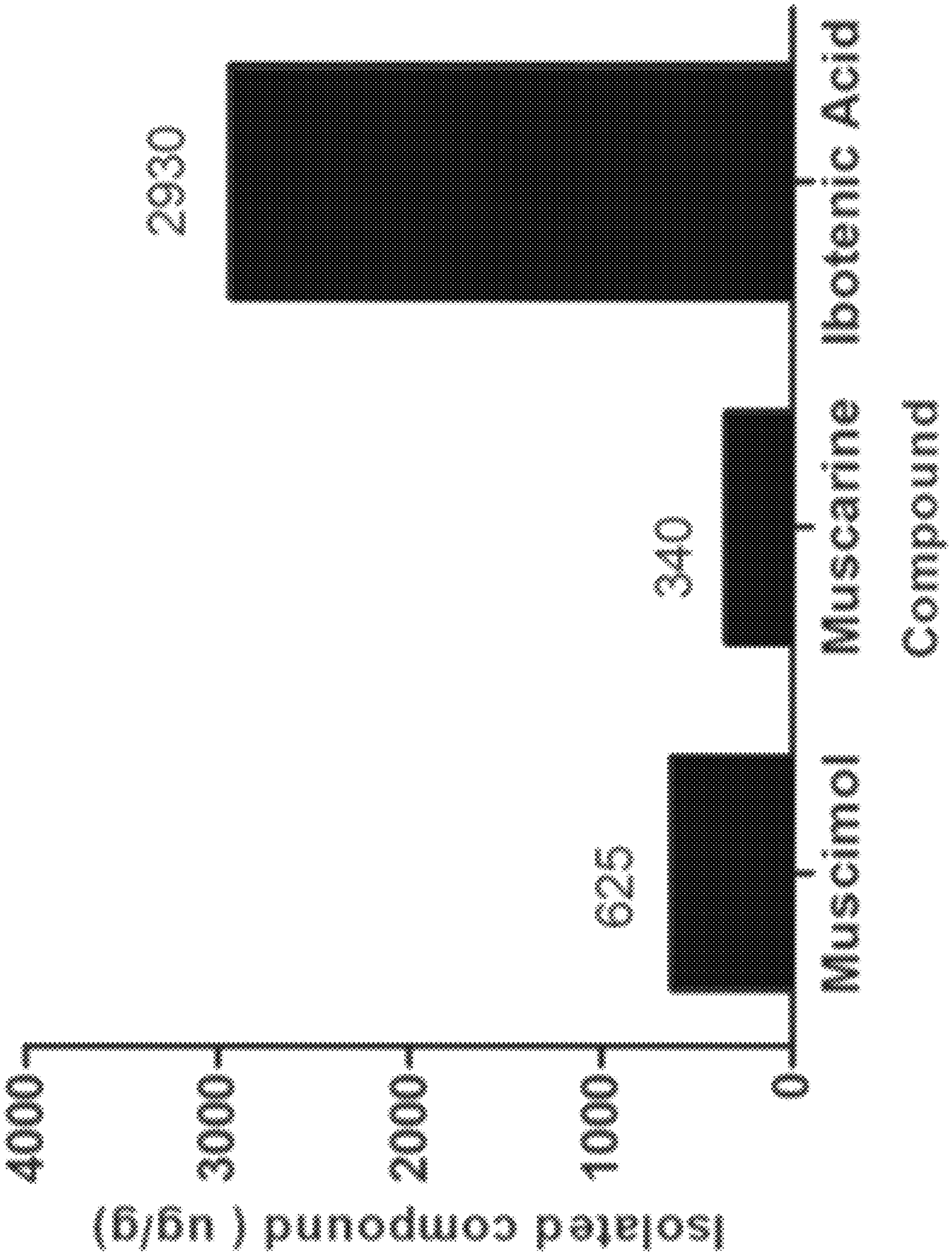
FIG. 7 is a graph of a quantitative analysis of heated and ground *Amanita muscaria* mushroom dry powder, as described as part of the process of FIG. 1.

High performance liquid chromatography tandem mass spectrometry ("HPLC-MS/MS") was used to analyze mushrooms and extracts at various stages of the process described in Example 1. FIG. 7 shows the muscimol (625 μg/g), muscarine (340 μg/g), and ibotenic acid (2930 μg/g) content of dried/heated and ground *Amanita muscaria* mushrooms, the starting material for the described extraction processes.

Figure 2:
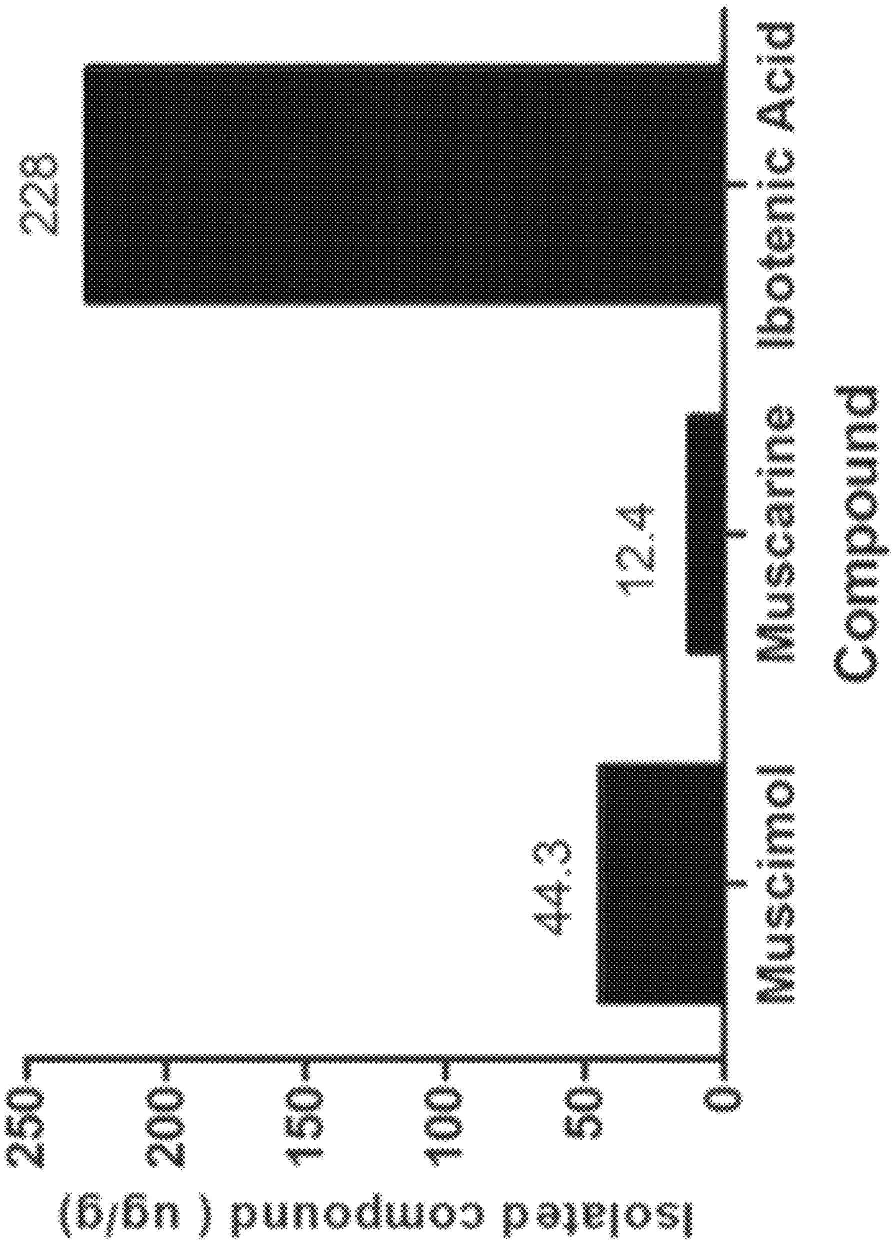
FIG. 2 is a graph of a quantitative analysis of *Amanita muscaria* isolated extract after acidification and before distillation (i.e., at time 0), in the process of FIG. 1.

FIGS. 2-5 show the results of quantitative HPLC-MS/MS analysis of mushroom extract at hourly timepoints of the 3 hour distillation. FIG. 2 shows a quantitative analysis of *Amanita muscaria* isolated extract after acidification and before distillation. The undistilled extract contained 44.3 μg/g muscimol, 12.4 μg/g muscarine, and 228 μg/g ibotenic acid.

Figure 3:
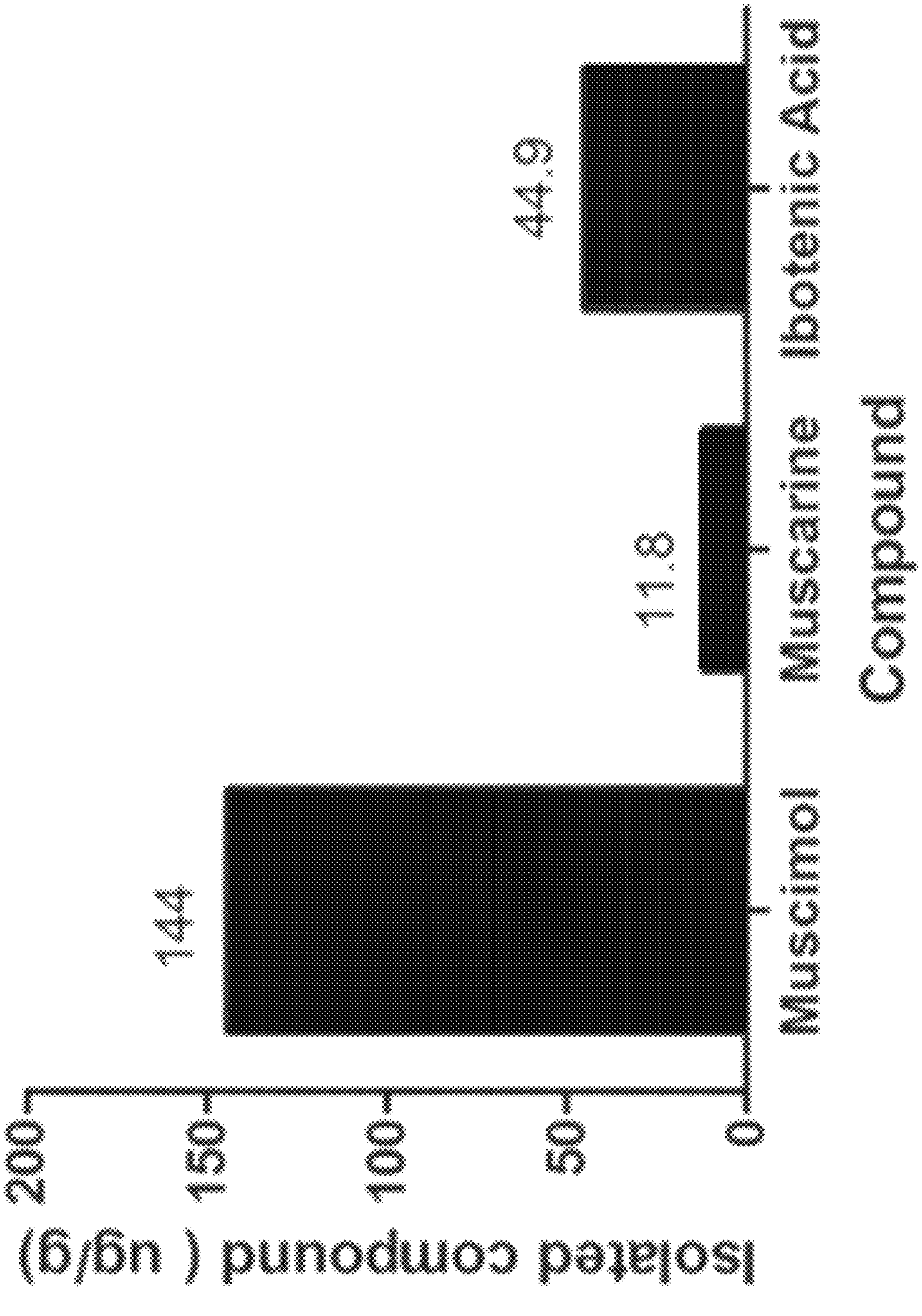
FIG. 3 is a graph of a quantitative analysis of the *Amanita muscaria* isolated extract after 1 hour of distillation, in the process of FIG. 1.

FIG. 3 shows the content of *Amanita muscaria* mushroom extract after 1 hour of distillation. Compared to the starting material, the amount of muscimol increased about three-fold (from 44.3 μg/g to 144 μg/g), while the amount of ibotenic acid substantially decreased (from 228 μg/g to 44.9 μg/g).

Figure 4:
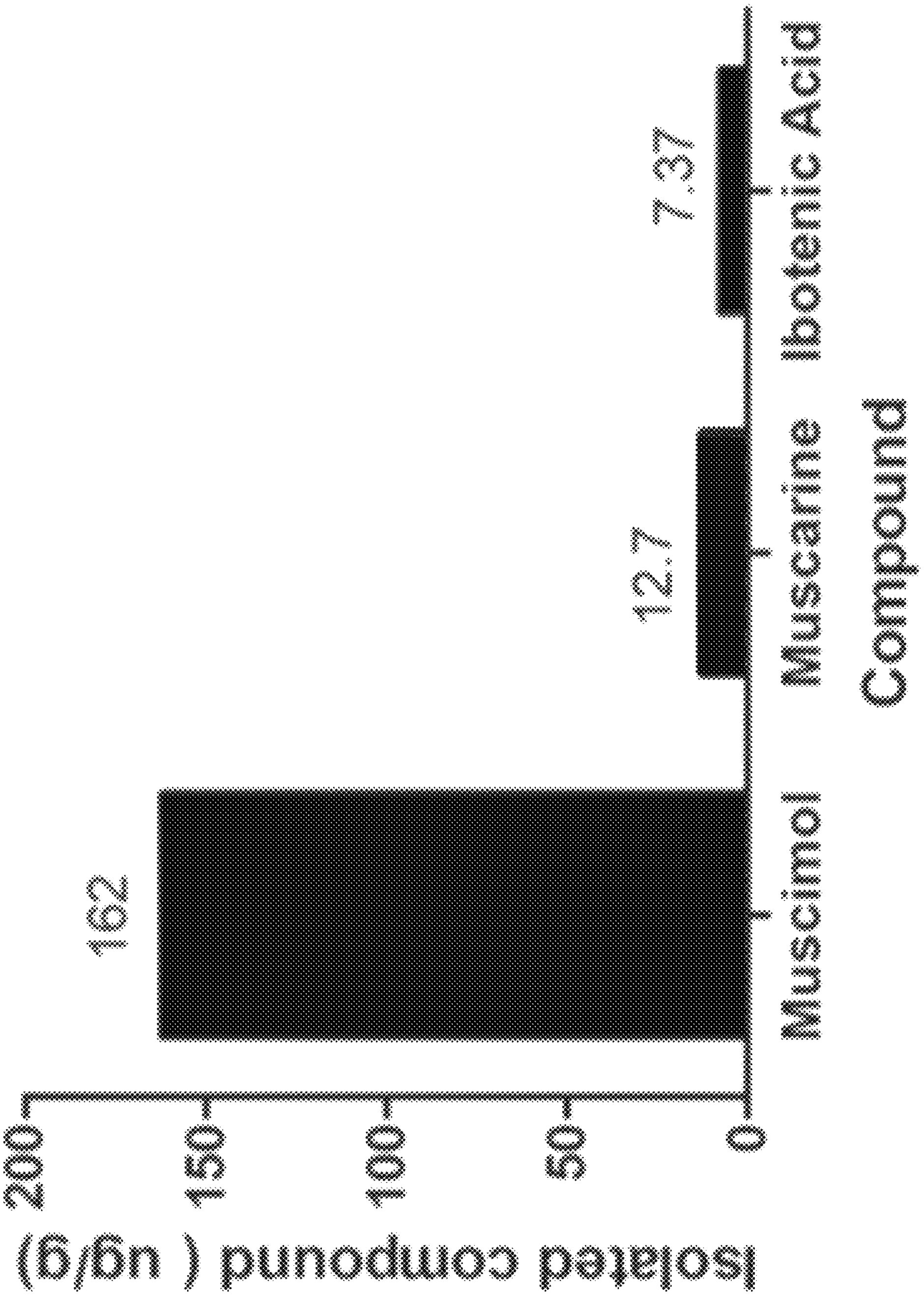
FIG. 4 is a graph of a quantitative analysis of the *Amanita muscaria* isolated extract after 2 hours of distillation, in the process of FIG. 1.

FIG. 4 shows a quantitative analysis of the *Amanita muscaria* isolated extract after 2 hours of distillation. This process further increased levels of muscimol to 162 μg/g. Ibotenic acid levels continued to decline (7.37 μg/g), while the amount of muscarine remained comparable to levels observed at 1 hour (12.7 μg/g).

Figure 5:
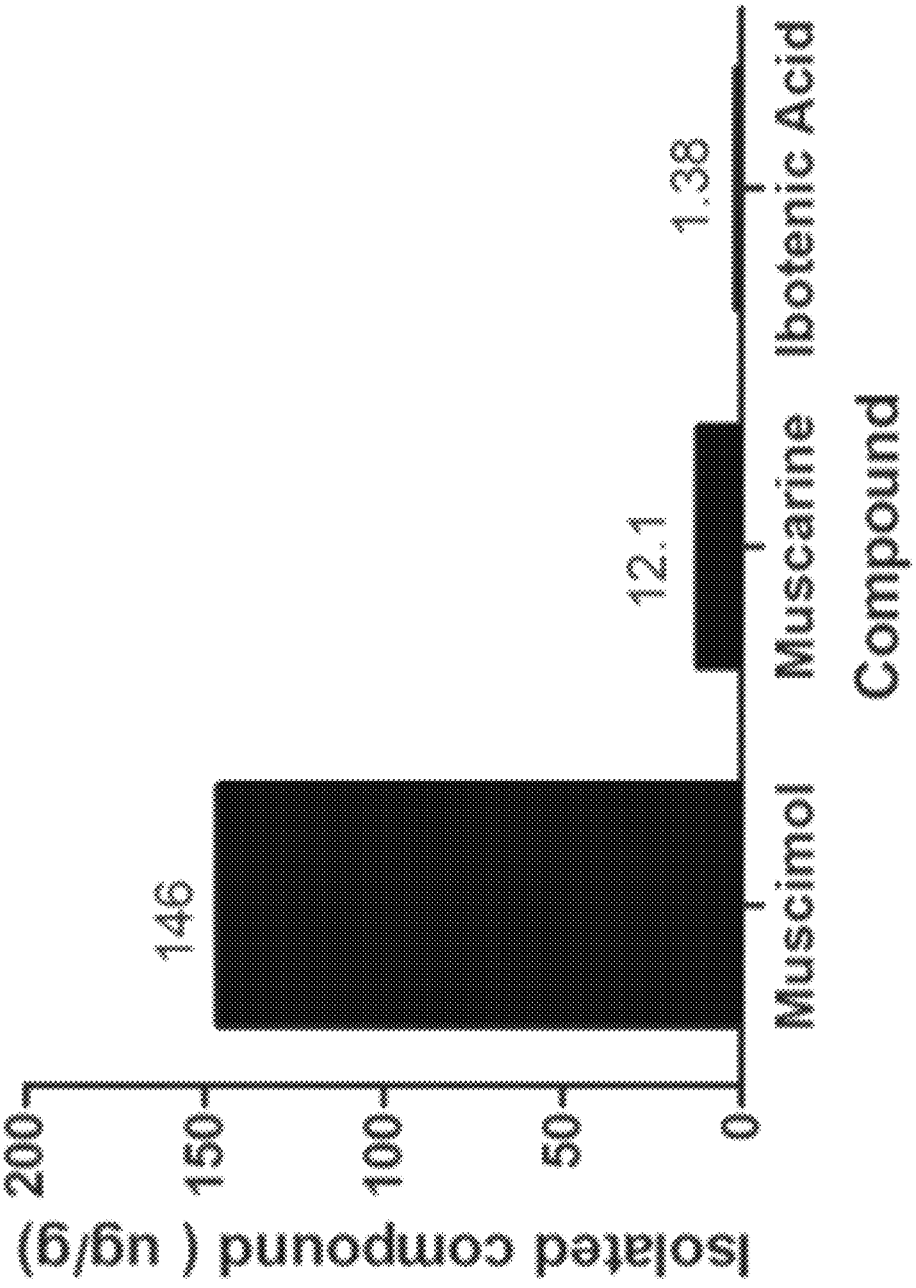
FIG. 5 is a graph of a quantitative analysis of the *Amanita muscaria* isolated extract after 3 hours of distillation, in the process of FIG. 1.

FIG. 5 shows a quantitative analysis of the *Amanita* isolated extract after 3 hours of distillation. Levels of muscimol were observed to decrease from determinations at 2 hours of distillation (from 162 μg/g to 146 μg/g). Levels of muscarine remained comparable to previous determinations made after acidification (12.1 μg/g), and ibotenic acid levels further decreased to 1.38 μg/g.

In summary, HPLC-MS/MS analysis was used to compare raw material, dried and ground *Amanita muscaria* mushrooms, to mushroom extract at hourly time points along the distillation process. The muscimol content in the ground mushroom powder was 625 micrograms per gram decreased in response to processing (44.3 μg/g) but increased significantly with distillation time (162 μg/g at 2 hours of distillation). The mushrooms' ibotenic acid content continually decreased throughout processing and distillation, reaching levels as low as 1.38 μg/g (from 2930 μg/g in raw material). Muscimol content was observed to decline from 2 hours of distillation to 3 hours of distillation, but the decrease was small, and the ibotenic acid decreased to an advantageous de minimis amount. It will be readily appreciated that the product can only be distilled to a certain limit before it reaches a saturation point. Additionally, original muscarine content also decreased due to processing but remained at low levels throughout the distillation process (~12 μg/g).

Quantitative analyses of the cadmium, arsenic, mercury, and lead content of the mushrooms of Example 1 were also performed by inductively coupled plasma mass spectrometry ("ICPMS"). The cadmium content of the heated, ground mushroom powder was found to be 10.2 parts per million ("PPM"), the arsenic content was found to be 1.67 PPM, the mercury content was found to be 1.18 PPM, and the lead content was found to be 0.865 PPM. Prior to the start of reflux, the cadmium content was found to be 0.073 parts per million ("PPM"), the arsenic content was found to be 0.018 PPM, the mercury content was found to be undetected (less than 0.001 PPM), and the lead content was found to be 0.011 PPM, which are significant improvements. It will be appreciated that the heavy metals are reduced from the initial step of washing in the water to the refluxing step.

TABLE 1

| Parameter | Specification | Method |
|---|---|---|
| Color | Brown | Organoleptic |
| Taste | Similar to meat gravy | Organoleptic |
| Smell | Forest mushroom scent | Organoleptic |
| Muscimol | <18,000 μg/g | Non-compendial in-house method (HPLC-MS/MS) |
| Muscarine | <600 μg/g | Non-compendial in-house method (HPLC-MS/MS) |
| Ibotenic Acid | <20 μg/g | Non-compendial in-house method (HPLC-MS/MS) |
| Stizolobinic Acid | Not detected | Non-compendial in-house method (HPLC-MS/MS) |
| Arsenic | <0.03 ppm | EPA 3052 (HPLC-MS/MS) |
| Cadmium | <0.09 PPM | EPA 3052 (HPLC-MS/MS) |
| Mercury | <0.02 PPM | EPA 3052 (HPLC-MS/MS) |
| Lead | <0.09 PPM | EPA 3052 (HPLC-MS/MS) |
| Pesticides | Conforms | Conforms |

TABLE 2

| Compound | USP 561 Maximum Residue Limit (ppm) | Results (pass/fail) |
|---|---|---|
| Acephate | 0.1 | Pass |
| Alachlor | 0.05 | Pass |
| Aldrin and dieldrin (sum of) | 0.05 | Pass |
| Azinphos-ethyl | 0.1 | Pass |
| Azlnphos-methyl | 1 | Pass |
| Bromophos-ethyl | 0.05 | Pass |
| Bromophos-methyl | 0.05 | Pass |
| Bromopropylate | 3.00 | Pass |
| Chlordane (sum of cis-, trans-, and oxychlordane) | 0.05 | Pass |
| Chlorfenvinphos | 0.50 | Pass |
| Chlorpyriphos-ethyl | 0.2 | Pass |
| Chlorpyriphos-methyl | 0.1 | Pass |
| Chlorthals-dimethyl | 0.01 | Pass |
| Cyfluthrin (sum of) | 0.1 | Pass |
| A-cyalothtrin | 1 | Pass |
| Cypermethrin and isomers (sum of) | 1 | Pass |
| DDT (sum of o,p'- DDE, pp'- DDE, o,p'- DDT, p,p-DDT, o,p'TDE, and p,p'- TOE) | 1 | Pass |
| Deltamethrin | 0.5 | Pass |
| Diazinon | 0.5 | Pass |
| Dichlofluanid | 0.1 | Pass |

TABLE 2-continued

| Compound | USP 561 Maximum Residue Limit (ppm) | Results (pass/fail) |
|---|---|---|
| Dichlorvos | 1 | Pass |
| Dicofol | 0.5 | Pass |
| Dimethoate and omethoate (sum of) | 0.1 | Pass |
| Dithiocarbamates (expressed as CS2) | 2 | Pass |
| Endosulfan (sum of isomers and endosulfan sulphate) | 3 | Pass |
| Endrin | 0.05 | Pass |
| Ethion | 2 | Pass |
| Etrlmphos | 0.05 | Pass |
| Fenchlorophos (sum of fenchlorophos and fenchlorophos-oxon) | 0.1 | Pass |
| Fenitrothion | 0.5 | Pass |
| Fenpropathrin | 0.03 | Pass |
| Fensulfothion | 0.05 | Pass |
| Fenthion | 0.05 | Pass |
| Fenvalerate | 1.5 | Pass |
| Flucytrlnate | 0.05 | Pass |
| t-Fluvalinate | 0.05 | Pass |
| Fonophos | 0.05 | Pass |
| Heptachlor (sum of heptachlor, cis-heptachloroxide, and trans- heptachlorepoxide) | 0.05 | Pass |
| Hexachlorobenzene | 0.1 | Pass |
| Hexachlorocyclohexane (sum of isomers a-, -b, -d, -e) | 0.3 | Pass |
| Lindane (g-hexachlorocydohexane) | 0.6 | Pass |
| Malathion and malaxon (sum of) | 1 | Pass |
| Mecarbam | 0.05 | Pass |
| Methacriphos | 0.05 | Pass |
| Methamidophos | 0.05 | Pass |
| Methidathion | 0.2 | Pass |
| Methoxychlor | 0.05 | Pass |
| Mlrex | 0.01 | Pass |
| Monocrotophos | 0.1 | Pass |
| Parathion-ethyl and Paraoxon-ethyle (sum of) | 0.5 | Pass |
| Parathion-methyl and Paraoxon-methyle (sum of) | 0.2 | Pass |
| Pendimethalin | 0.1 | Pass |
| Pentachloranisol | 0.01 | Pass |
| Permethrin and isomers (sum of) | 1 | Pass |
| Phosalone | 0.1 | Pass |
| Phosmet | 0.05 | Pass |
| Piperonyl butoxide | 3 | Pass |
| Pirimiphos-ethyl | 0.5 | Pass |
| Pirimiphos-methyl (sum of pirimiphos-methyl and N-desethyl-pirlmlphos- methyl) | 4 | Pass |
| Procymidone | 0.1 | Pass |
| Profenophos | 0.1 | Pass |
| Prothiophos | 0.05 | Pass |
| Pyrethrum | 3 | Pass |
| Quinalphos | 0.05 | Pass |
| Quintozene | 1 | Pass |
| S-421 | 0.02 | Pass |
| Tecnazene | 0.05 | Pass |
| Tetradifon | 0.3 | Pass |
| Vinclozolin | 0.4 | Pass |

Certificates of Analysis for four batches of *Amanita muscaria* extract resulting from the process of Example 1 are summarized in Table 3, Table 4, Table 5, and Table 6 below. The four batches meet all the testing specifications in Table 1 and Table 2. Further, Table 7 illustrates the potency of the resultant product submitted with lot number 0001, highlighted in Table 3 below, and similar potency percentages for muscimol, ibotenic acid, and the other compounds discussed herein, as well as purity percentages for all such compounds, may be calculated for other batches of extracts herein, as well as any extracts prepared according to the methods of the invention, based on the teachings herein and the ordinary skill in the art.

TABLE 3

| Product Name: | Amanita muscaria Extract | Product Lot Number: | 0001 |
|---|---|---|---|
| Report Date: | 12/07/2020 | Laboratory Number: | 7809405373 |
| Extract Amount: | 120 g | Batch Release Date: | December 7, 2020 |
| Description Assay | Method | Result | Pass or Fail |
| Muscimol | Non-compendial in-house method by HPLC-MS/MS | 16922 μg/g | Pass |
| Muscarine | Non-compendial in-house method by HPLC-MS/MS | 1468 μg/g | Pass |
| Ibotenic Acid | Non-compendial in-house method by HPLC-MS/MS | 159 μg/g | Pass |
| Cadmium | EPA 3052 | 0.14 μg/g | Pass |
| Arsenic | EPA 3052 | 2.5 μg/g | Pass |
| Mercury | EPA 3052 | 0.12 μg/g | Pass |
| Lead | EPA 3052 | 1.6 μg/g | Pass |

TABLE 4

| Product Name: | Amanita muscaria Extract | Product Lot Number: | 0002 |
|---|---|---|---|
| Report Date: | 14/04/2021 | Laboratory Number: | 7809405373 |
| Extract Amount: | 20 g | Batch Release Date: | April 22, 2021 |
| Description Assay | Method | Result | Pass or Fail |
| Muscimol | Non-compendial in-house method by HPLC-MS/MS | 146 μg/g | Pass |
| Muscarine | Non-compendial in-house method by HPLC-MS/MS | 12.1 μg/g | Pass |
| Ibotenic Acid | Non-compendial in-house method by HPLC-MS/MS | 1.38 μg/g | Pass |
| Cadmium | EPA 3052 | 0.073 μg/g | Pass |
| Arsenic | EPA 3052 | 0.018 μg/g | Pass |
| Mercury | EPA 3052 | ND | Pass |
| Lead | EPA 3052 | 0.011 μg/g | Pass |

TABLE 5

| Product Name: | Amanita muscaria Extract | Product Lot Number: | 0003 |
|---|---|---|---|
| Report Date: | July 2, 2021 | Laboratory Number: | 7809405373 |
| Extract Amount: | 4,300 g/ solid | Batch Release Date: | July 5, 2021 |
| Description Assay | Method | Result | Pass or Fail |
| Muscimol | Non-compendial in-house method by HPLC-MS/MS | 2800.356 μg/g Specification <18,000 μg/g | Pass |
| Muscarine | Non-compendial in-house method by HPLC-MS/MS | 499.453 μg/g Specification <600 μg/g | Pass |
| Ibotenic Acid | Non-compendial in-house method by HPLC-MS/MS | 14.953 ug/g Specification <20 μg/g | Pass |
| Cadmium | EPA 3052 | 0.20 μg/g | Pass |
| Arsenic | EPA 3052 | ND | Pass |
| Mercury | EPA 3052 | 0.14 μg/g | Pass |
| Lead | EPA 3052 | 0.019 μg/g | Pass |
| Stizolobinic acid | Non-compendial | ND | Pass |

TABLE 5-continued

| | | | |
|---|---|---|---|
| | in-house method by HPLC-MS/MS | | |

TABLE 6

| Product Name: | Amanita muscaria Extract | Product Lot Number: | 0004 |
|---|---|---|---|
| Report Date: | July 30, 2021 | Laboratory Number: | 7809405373 |
| Extract Amount: | 200 grams/ paste | Batch Release Date: | July 31, 2021 |
| Description Assay | Method | Result | Pass or Fail |
| Muscimol | Non-compendial in-house method by HPLC-MS/MS | 1829.467 μg/g Specification <18,000 μg/g | Pass |
| Muscarine | Non-compendial in-house method by HPLC-MS/MS | 359.567 μg/g Specification <600 μg/g | Pass |
| Ibotenic Acid | Non-compendial in-house method by HPLC-MS/MS | 12.867 μg/g Specification <20 g/g | Pass |
| Cadmium | EPA 3052 | 0.98 μg/g | Pass |
| Arsenic | EPA 3052 | 0.014 μg/g | Pass |
| Mercury | EPA 3052 | 0.36 μg/g | Pass |
| Lead | EPA 3052 | 0.017 μg/g | Pass |
| Stizolobinic acid | Non-compendial in-house method by HPLC-MS/MS | ND | Pass |

TABLE 7

| | |
|---|---|
| Test Item Name: | *Amanita muscaria* Extract |
| Purity/Assay: | 1.69% muscimol, 0.15% muscarine, 0.02% ibotenic acid (potency) |
| Batch produced by: | Psyched Wellness |
| Color: | Tan |
| Physical Characteristics: | Powder, pH-3.0, water soluble |
| Quantity sent: | 120 g |
| Storage condition: | Room temperature (22° C.), long term storage (−20° C.) |

An independent review panel of scientific experts has concluded that *Amanita muscaria* extract in accordance with the first embodiment of the invention, and having compositions in accordance with Tables 3-7 above, is Generally Recognized As Safe ("GRAS") as a bulk ingredient for a variety of finished conventional food products, including for use in the general adult population greater than 18 years of age, except for pregnant women and lactating women ("the target population"). *Amanita muscaria* extract in accordance with the first embodiment of the invention is GRAS in the target population for use as beverage powders and in ready-to-drink beverages at a maximum total daily serving size of 872 mg/person/day, which contains 2.89 mg/per/day of muscimol, muscarine, and ibotenic acid (referred to as an "Alkaloid Blend" or "AMAB." *Amanita muscaria* extract in accordance with the first embodiment of the invention is GRAS for use in dietary supplements in the target population greater at a maximum total daily serving size of 880 mg/person/day, which contains 2.917 mg/person/day AMAB.

Example 2

Example 2 is another example of an embodiment, such as the first embodiment. *Amanita muscaria* mushrooms are identified and harvested by hand by cutting off the stipe and placing the fresh caps into a container. The mushrooms are then transported to a processing facility. The mushrooms are air-dried in a forced air food dryer at +50° C. for 24-48 hrs. Mushrooms are considered dry when they snap in half and are "cracker dry" (dehydrated *Amanita muscaria* moisture content will range from 4%-7% on a dry weight basis). Over drying the mushrooms results in loss of potency. Muscimol is an unstable compound. Therefore, the mushrooms are removed from dehydrators when the mushrooms reach the target moisture content of 4%-7% on a dry weight basis. Dehydrated mushrooms are sealed in plastic bags or other airtight containers and stored in darkness at −15° C. until final processing. If the mushrooms are shipped to the processing location within 5 days, the mushrooms can be stored at 3° C. Prolonged storage at +20° C. or +3° C. results in loss of potency and gradual destruction of the mushrooms by macroscopic and microscopic organisms. The mushrooms are shipped sealed in plastic bags in quantities of 1 kg to 3 kg inside boxes sized for the quantity of mushrooms being shipped.

In the first step of processing to produce the aqueous extract, the dried caps are ground to a fine powder using a food grinder or food processor (at room temperature). Prior to continuing the extraction protocol, the mushrooms must pass quality assurance tests. A small batch of each preparation undergoes analysis to ensure the amount of muscimol, muscarine and ibotenic acid fall within safety and production specifications. In addition to the aforementioned, other parameters assayed for before extraction include heavy metals and pesticides. This is followed by extraction of each tested mushroom. A volume of 7000 ml distilled water is heated to 75° C., to which mushroom powder is added. The mixture is stirred constantly at 1120 rpm (75° C.) for 1 hour. Subsequently, the aqueous mushroom mixture is filtered through a filter press (75 μm nylon filter bag) and pressed slowly over 60 min. This step is performed slowly, as pressing too fast or with too much pressure can cause the filter bag to balloon and break apart inside the filter press chamber.

In the next step, the filtrate is centrifuged (4000 rpm, room temperature) for 15 min and the pellet is discarded. The collected supernatant is placed in a large beaker and stirred while the pH is adjusted to 2.5 using 3 M HCl (0.1-0.3%). The amount of HCl needed will range on the volume.

Next, the supernatant is concentrated by heating under pressure (250° F. at 15 psi) for 40 min (time depends on the volume). The distillation system described above may be used, for example. The resulting extract may then be analyzed and bottled. The method described herein allows for a more rapid extraction of larger volumes as compared to the methods of Example 1.

Table 1 above shows examples of the testing specifications and test methods for *Amanita muscaria* extract made in accordance with embodiments of the invention, as described in embodiment 1 (Examples 1 and 2). *Amanita muscaria*, similar to other edible mushrooms, are considered to be strong bio-accumulators of heavy metals in soil (Demirbaş, Food Chemistry, 2001; 74(3): 293-301). Acceptable specifications for muscimol, muscarine, ibotenic acid, stizolobinic acid, and the heavy metals arsenic, cadmium, mercury, and lead are shown. In this example testing specification, the *Amanita muscaria* extract comprises less than 18 mg/g of muscimol, less than 600 μg/g muscimol, and less than 20 μg/g ibotenic acid. In addition, in this example testing specification, no more than 0.09 ppm, 0.03 ppm, 0.09 ppm and 0.02 ppm of cadmium, arsenic, lead and mercury, respectively. The presence of stizolobinic acid is indicative of the presence of *Amanita* pantherina, which is toxic and thus identifies the incorrect *Amanita* mushroom. In this example testing specification, no stizolobinic acid can be present. Pesticides are indicated as conforming. Table 2, above, shows the testing specifications for a full panel of pesticides in accordance with USP 561. The limits for all tested pesticides were met.

Example 3

Example 3 is an example of the second embodiment of the invention. In Example 2, a different filtration process is provided to increase yield as compared to the first embodiment of the invention and Example 1. In this example, the same *Amanita muscaria* ("mushrooms") as in Example 1 were pressed through a filter to obtain filtered extract.

A total amount of 1.5 kg of mushrooms were inspected and dehydrated, as in Example 1, and then cut into pieces having dimensions of about 1 cm×1 cm. The pH of distilled water was confirmed to be about 7 by a calibrated pH meter and the water was boiled for 10 minutes, as in Example 1. The cut pieces of the mushrooms were placed in the boiled water. The temperature of the water was maintained at 95° C.

Instead of the vacuum filtration process of Example 1, a fruit press was used to press the mushrooms through a filter to extract filtrate in this Example. A 1 L beaker was added to the bottom of the fruit press to collect the filtrate. Twenty-five grams of the heated mushroom pieces were added to a 125-micron filter bag having a volume of 40 liters. The fruit press was a 1.3 liter standard aluminum and stainless steel press, available commercially and sourced online, and like fruit presses will be able to be used without material modifications to the process herein.

The filter bag containing mushroom pieces was placed in the fruit press and the pressure of the fruit press was increased in about 5 minute increments over the course of 1 hour, to press the mushroom pieces through the filter bag. The process was repeated with a second bag containing 25 grams of the heated mushroom pieces. 14-15 liters of filtrate were collected having a moisture content of from about 50% to about 70%. A moisture meter was used to analyze content. As described herein, following filtration, the extract was acidified.

The filtrate was placed in a Pyrex beaker, placed on a heating plate in a microwave oven, and heated at 100% power for 2 hours to reduce the volume to 10% of the original amount, as measured with the Pyrex beaker.

After heating, the filtrate on visual inspection was thick and colored black, and it was therefore determined that the filtrate needed to be further dried or cured. The filtrate was heated again in the microwave oven at 80% power at one minute intervals, with stirring in between, for a total of one hour, until the color of the filtrate turned from black to light brown, demonstrating the desired change in moisture content. The resulting filtrate had a thick appearance on visual inspection, and was similar in physical consistency to bread dough upon tactile inspection.

Figure 11:
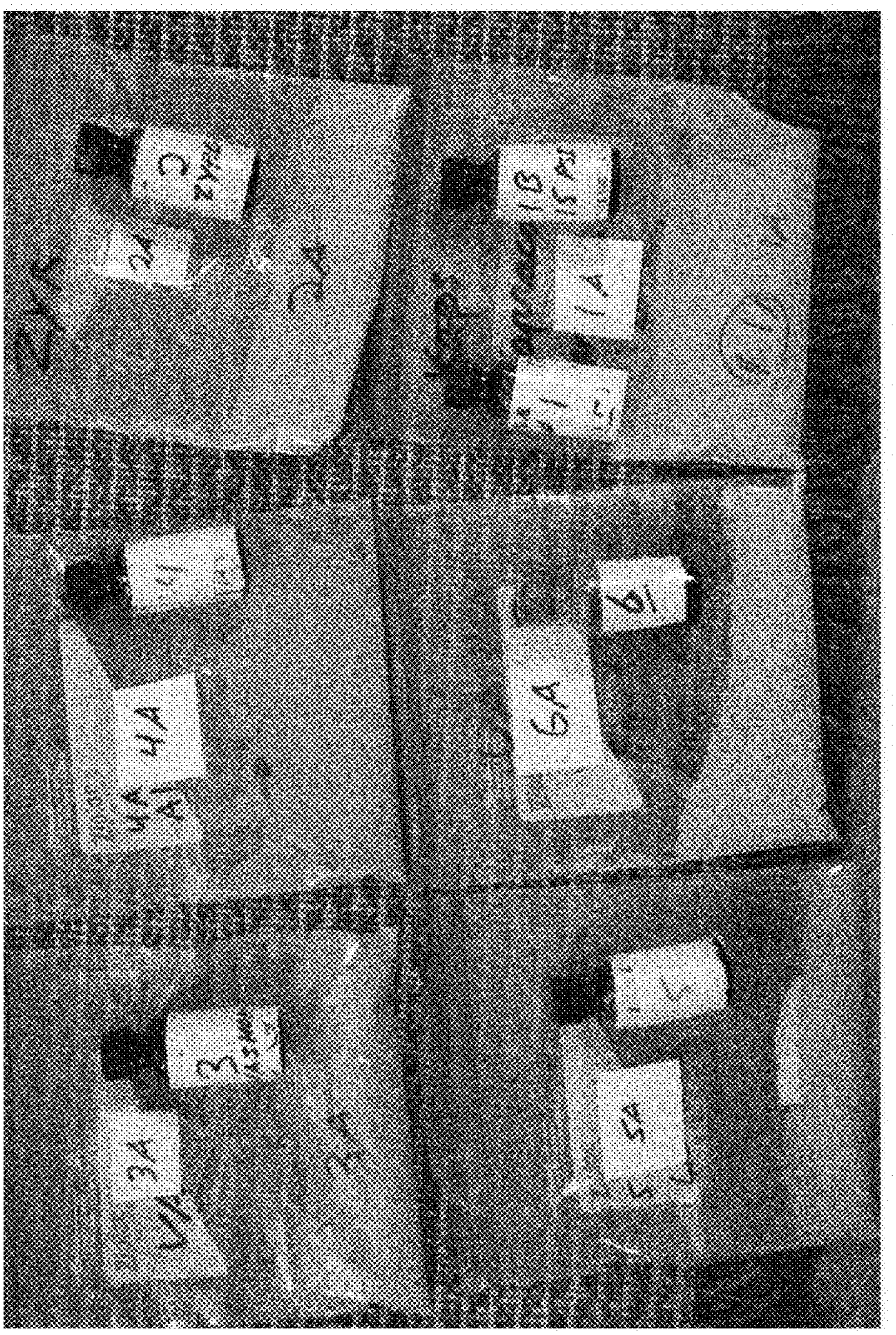
FIG. 11 is an image of examples of finely ground mushroom powder in plastic bags, wherein the bags are further labeled to differentiate between the contents of each bag.

As the filtrate was cooling, the filtrate was cut into pieces having a length and width of from about 3 cm to about 4 cm. Each piece was ground into a fine powder using a coffee grinder, to a level visually similar to that described and depicted in the example of FIG. 10. The ground power was placed into a sealed plastic bag (as depicted), which was stored in the dark at −15° C., as shown in FIG. 11, for example. The levels of muscimol and ibotenic acid obtained from the methods in this Example were comparable to those produced by the previous methods, which yielded a liquid extract. Advantages of a dried extract include ease of storage and enhanced storage stability.

The foregoing description, for purposes of explanation, uses specific nomenclature to provide a thorough understanding of embodiments of the invention. However, it will be apparent to one skilled in the art that specific details are not required in order to practice embodiments of the invention. Thus, the foregoing description of specific embodiments of the invention is presented for purposes of illustration and description. It is not intended to be exhaustive or to limit the invention to the precise forms disclosed; obviously, many modifications and variations are possible in view of the above. The embodiments were chosen and described in order to best explain the principles of the invention and its practical applications, through the elucidation of specific examples, and to thereby enable others skilled in the art to best utilize the invention and various embodiments with various modifications as are suited to the particular use contemplated, when such uses are beyond the specific examples disclosed. Accordingly, the scope of the invention shall be defined solely by the following claims and their equivalents.

What is claimed is:

1. A method of obtaining an *Amanita muscaria* mushroom extract having a reduced ibotenic acid content, comprising:

a. selecting *Amanita muscaria* mushroom biomass for extraction;

b. performing an aqueous extraction of the biomass to produce an extract;

c. reducing the pH of the extract to between about 2.0 to about 4.0;

d. refluxing the acidified extract; and e. distilling the refluxed extract;

wherein the method decreases the ibotenic acid content of the extract and increases the muscimol content of the extract.

2. The method of claim 1, wherein the biomass is ground into a powder prior to the aqueous extraction.

3. The method of claim 1, wherein the biomass is dried to a moisture content of about 1% to about 10%, about 2% to about 7%, about 4% to about 7%, or about 2%, about 3%, or about 4%, prior to the aqueous extraction.

4. The method of claim 1, wherein the aqueous extraction is performed in water heated to between 65° C. to 120° C., 70° C. to 100° C., or 75° C. to 95° C., for a period of about 0.5 hours to about 3 hours, wherein each range is inclusive.

5. The method of claim 4, wherein the water temperature is maintained at about 75° C. or about 95° C. for about 1 hour or at least 1 hour.

6. The method of claim 1, wherein the pH is reduced to about 2.0, about 2.5, or about 3.0.

7. The method of claim 1, wherein the refluxing is performed using a condenser under light-protected conditions.

8. The method of claim 1, wherein the distilling is performed at a pressure of between about 15 psi to about 25 psi (about 1.0 to about 1.7 bar) and at a temperature of between about 200° F. to about 350° F. (about 93° C. to about 177° C.).

9. The method of claim 1, wherein the distilling proceeds for between about 0.5 hours to about 4 hours, or for about 1 hour, about 2 hours, about 3 hours, or about 4 hours.

10. The method of claim 1, wherein the method yields an extract comprising no stizolobinic acid and no more than 0.09 ppm of cadmium, 0.03 ppm of arsenic, 0.09 ppm of lead, and 0.02 ppm of mercury.

11. The method of claim 1, wherein selecting the biomass for extraction comprises subjecting the biomass to chemical analysis.

12. The method of claim 11, wherein the chemical analysis comprises testing for the presence of *Amanita pantherina* in the biomass.

13. The method of claim 12, wherein testing for the presence of *Amanita pantherina* in the biomass comprises determining the concentration of stizolobinic acid in the biomass.

14. The method of claim 1, wherein the method yields an extract comprising muscimol and ibotenic acid in a ratio of between about 3:1 and about 150:1, or between about 10:1 and about 15:1.

15. The method of claim 1, wherein the method yields an extract comprising muscimol and ibotenic acid in a ratio of at least 100:1.

16. The method of claim 1, wherein the method yields an extract comprising less than 250 μg/g of ibotenic acid.

17. The method of claim 16, wherein the method yields an extract comprising less than 20 μg/g of ibotenic acid.

* * * * *